(12) United States Patent
Jung et al.

(10) Patent No.: US 9,101,263 B2
(45) Date of Patent: Aug. 11, 2015

(54) ACQUISITION AND ASSOCIATION OF DATA INDICATIVE OF AN INFERRED MENTAL STATE OF AN AUTHORING USER

(75) Inventors: Edward K. Y. Jung, Bellevue, WA (US);
Eric C. Leuthardt, St. Louis, MO (US);
Royce A. Levien, Lexington, MA (US);
Robert W. Lord, Seattle, WA (US);
Mark A. Malamud, Seattle, WA (US);
John D. Rinaldo, Jr., Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1844 days.

(21) Appl. No.: 12/215,683

(22) Filed: Jun. 26, 2008

(65) Prior Publication Data
US 2009/0292702 A1 Nov. 26, 2009

Related U.S. Application Data

(63) Continuation-in-part of application No. 12/154,686, filed on May 23, 2008, now Pat. No. 7,904,507, and a continuation-in-part of application No. 12/157,611, filed on Jun. 10, 2008.

(51) Int. Cl.
*G06F 17/30* (2006.01)
*A61B 5/00* (2006.01)
*G06Q 10/10* (2012.01)
*H04L 12/58* (2006.01)

(52) U.S. Cl.
CPC ............ *A61B 5/0002* (2013.01); *G06Q 10/107* (2013.01); *H04L 12/58* (2013.01)

(58) Field of Classification Search
USPC .................................. 707/705, 736, 756, 758
See application file for complete search history.

(56) References Cited

U.S. PATENT DOCUMENTS

| | | |
|---|---|---|
| 5,715,374 A | 2/1998 | Heckerman et al. |
| 5,724,698 A | 3/1998 | Mondragon |
| 5,724,968 A | 3/1998 | Iliff |
| 5,740,549 A | 4/1998 | Reilly et al. |
| 5,761,512 A | 6/1998 | Breslau et al. |
| 6,113,540 A | 9/2000 | Iliff |
| 6,190,314 B1 | 2/2001 | Ark et al. |
| 6,523,009 B1 | 2/2003 | Wilkins |
| 6,573,927 B2 | 6/2003 | Parulski et al. |
| 6,591,296 B1 | 7/2003 | Ghanime |
| 7,300,402 B2 | 11/2007 | Iliff |
| 7,406,307 B2 | 7/2008 | Manto |
| 7,483,899 B2 | 1/2009 | Berry et al. |

(Continued)

OTHER PUBLICATIONS

Parc Research; "Content-Centric Networking: PARC's Strategy for Pioneering a Self-Organizing Network That Meets Information Needs"; pp. 1-4; Xerox Corporation; located at: http://www.parc.xerox.com/research/projects/networking/contentcentric/mediabackgrounder.html; printed on Mar. 2, 2009.

(Continued)

*Primary Examiner* — Hares Jami

(57) ABSTRACT

A computationally implemented method includes, but is not limited to: acquiring data indicative of an inferred mental state of an authoring user; and associating the data indicative of the inferred mental state of the authoring user with an electronic message. In addition to the foregoing, other method aspects are described in the claims, drawings, and text forming a part of the present disclosure.

6 Claims, 11 Drawing Sheets

(56) References Cited

U.S. PATENT DOCUMENTS

| | | | |
|---|---|---|---|
| 7,512,889 | B2 | 3/2009 | Newell et al. |
| 7,529,674 | B2 | 5/2009 | Gong et al. |
| 7,698,255 | B2 | 4/2010 | Goodwin et al. |
| 7,720,784 | B1 | 5/2010 | Froloff |
| 7,753,795 | B2 | 7/2010 | Harris et al. |
| 7,933,897 | B2 | 4/2011 | Jones et al. |
| 8,005,984 | B2 | 8/2011 | Campbell et al. |
| 2002/0065836 | A1 | 5/2002 | Sasaki |
| 2002/0095089 | A1* | 7/2002 | Yamamoto et al. ............ 600/476 |
| 2002/0135618 | A1 | 9/2002 | Maes et al. |
| 2002/0193670 | A1 | 12/2002 | Garfield et al. |
| 2003/0028647 | A1 | 2/2003 | Grosu |
| 2003/0037063 | A1 | 2/2003 | Schwartz |
| 2003/0139654 | A1 | 7/2003 | Kim et al. |
| 2003/0191568 | A1 | 10/2003 | Breed |
| 2003/0196171 | A1 | 10/2003 | Distefano, III |
| 2004/0001086 | A1 | 1/2004 | Brown et al. |
| 2004/0001090 | A1 | 1/2004 | Brown et al. |
| 2004/0230549 | A1 | 11/2004 | Freer et al. |
| 2004/0236236 | A1* | 11/2004 | Yanagidaira et al. ......... 600/509 |
| 2005/0010637 | A1 | 1/2005 | Dempski et al. |
| 2005/0078804 | A1 | 4/2005 | Yomoda |
| 2005/0283055 | A1 | 12/2005 | Shirai et al. |
| 2006/0010240 | A1 | 1/2006 | Chuah |
| 2006/0112111 | A1 | 5/2006 | Tseng et al. |
| 2006/0184464 | A1 | 8/2006 | Tseng et al. |
| 2006/0206833 | A1 | 9/2006 | Capper et al. |
| 2006/0221935 | A1 | 10/2006 | Wong et al. |
| 2006/0258914 | A1 | 11/2006 | Derchak et al. |
| 2007/0038054 | A1 | 2/2007 | Zhou et al. |
| 2007/0043590 | A1 | 2/2007 | Lee |
| 2007/0093965 | A1 | 4/2007 | Harrison et al. |
| 2007/0130112 | A1 | 6/2007 | Lin |
| 2007/0192038 | A1 | 8/2007 | Kameyama |
| 2008/0001600 | A1* | 1/2008 | deCharms ..................... 324/309 |
| 2008/0027984 | A1 | 1/2008 | Perdomo et al. |
| 2008/0059570 | A1* | 3/2008 | Bill .............................. 709/203 |
| 2008/0065468 | A1 | 3/2008 | Berg et al. |
| 2008/0096532 | A1 | 4/2008 | Lyle et al. |
| 2008/0114266 | A1 | 5/2008 | Shen et al. |
| 2008/0120129 | A1 | 5/2008 | Seubert et al. |
| 2008/0139889 | A1 | 6/2008 | Bagan |
| 2008/0146892 | A1 | 6/2008 | LeBoeuf et al. |
| 2008/0162393 | A1 | 7/2008 | Iliff |
| 2008/0162649 | A1 | 7/2008 | Lee et al. |
| 2008/0181381 | A1 | 7/2008 | Manto |
| 2008/0214903 | A1 | 9/2008 | Orbach |
| 2008/0215972 | A1 | 9/2008 | Zalewski et al. |
| 2008/0215973 | A1 | 9/2008 | Zalewski et al. |
| 2008/0235582 | A1 | 9/2008 | Zalewski et al. |
| 2008/0243825 | A1 | 10/2008 | Staddon et al. |
| 2009/0002178 | A1 | 1/2009 | Guday et al. |
| 2009/0030886 | A1 | 1/2009 | Pandeya |
| 2009/0055484 | A1 | 2/2009 | Vuong et al. |
| 2009/0063992 | A1 | 3/2009 | Gandhi et al. |
| 2009/0193344 | A1 | 7/2009 | Smyers |
| 2009/0251457 | A1 | 10/2009 | Walker et al. |
| 2009/0271375 | A1 | 10/2009 | Hyde et al. |
| 2010/0095362 | A1 | 4/2010 | Boberg et al. |
| 2010/0135369 | A1 | 6/2010 | Hagl et al. |

OTHER PUBLICATIONS

U.S. Appl. No. 13/135,462, Jung et al.
U.S. Appl. No. 12/931,359, Jung et al.
About.com.: Email Webpage; printed on Aug. 15, 2008; p. 1 located at http://email.about.com/gi/dynamic/offsite.htm?zi=1/XJ&sdn=email&zu=http%3A%2F%2Fwww.pointofmail.com%2F.
Ambler et al.; "Salience and Choice: Neural Correlates of Shopping Decisions"; Psychology & Marketing; Apr. 2004; pp. 247-261; vol. 21; No. 4; Wiley Periodicals, Inc.
Appenzeller et al.; "The Mobile People Architecture—Technical Report: CSL-TR-99-777"; Jan. 1999; pp. 1-10 (12 pages total incl. title page/abstract and copyright information); located at ftp://reports.stanford.edu/pub/cstr/reports/csl/tr/99/777/CSL-TR-99-777.pdf; Stanford University.
Bergman et al.; "A Personal Email Assistant"; HPInvent Website; printed on Aug. 15, 2008; pp. 1-22 (23 pages total incl. summary page); located at http://www.hpl.hp.com/techreports/2002/HPL-2002-236.pdf; Hewlett-Packard Company 2002.
Cabeza et al.; "Imaging Cognition II: An Empirical Review of 275 PET and fMRI Studies"; Journal of Cognitive Neuroscience; 2000; pp. 1-47; vol. 12; No. 1; Massachusetts Institute of Technology.
Centipaid.com; "Getting the Best Out of Surgemail's SPAM Features"; bearing dates of 2002-2006 and printed on Aug. 13, 2008; pp. 1-5; located at http://www.centipaid.com/en/support/surgemail.html; Centipaid Corporation.
Chance et al.; "A Novel Method for Fast Imaging of Brain Function, Non-Invasively, With Light"; Optics Express; May 11, 1998; pp. 411-423; vol. 2; No. 10; OSA.
Clearcontext; "User Guide"; bearing dates of 2003-2008 and printed on Aug. 15, 2008; pp. 1-4; located at http://www.clearcontext.com/user_guide/contacts.html; Clearcontext Corporation.
Communigatepro; "CommuniGate® Pro Version 5.1"; bearing dates of 1998-2007 and printed on Aug. 15, 2008; pp. 1-6; located at https://mx2.arl.org/Guide/default.html; Stalker Software, Inc.
Critical Path; "Critical Path: Putting Mobile Email in Context"; bearing a date of Aug. 11, 2005 and printed on Aug. 13, 2008; pp. 1-2; located at http://www.cbronline.com/article_feature.asp?guid=D9E4E0B0-BE6A-4928-8857-3A3682D852C1; CBR and CBRonline.com.
Goodmail Systems; "Certified Email: How it Works"; printed on Aug. 13, 2008; p. 1; located at http://www.goodmailsystems.com/products/certified-email/how_it_works.php.
Huang et al.; "Map Web: A Location-Based Converged Communications Platform"; Bell Labs Technical Journal—Lucent Technologies Inc.; 2006; pp. 159-171; Wiley Periodicals, Inc.
Inovalive: "iNovaLive: Email Solutions Through Email Evolution website"; bearing a date of 2006 and printed on Aug. 15, 2008; pp. 1-2; located at http://inovalive.com/site/index; iNovaSoft Ltd.
Kenning et al.; "NeuroEconomics: An Overview from an Economic Perspective"; Brain Research Bulletin; 2005; pp. 343-354; vol. 67; Elsevier Inc.
Lee et al.; "What is 'Neuromarketing'? A Discussion and Agenda for Future Research"; International Journal of Psychophysiology; bearing dates of 2006 and 2007; pp. 199-204; vol. 63; Elsevier B.V.
Matthews et al.; "Applications of fMRI in Translational Medicine and Clinical Practice"; Nature Reviews/Neuroscience; Sep. 2006; pp. 732-744; vol. 7; Nature Publishing Group.
Murphy, Kevin; "Pay-Per-Email Scheme Draws Critics"; bearing a date of Feb. 7, 2006 and printed on Aug. 13, 2008; pp. 1-3; located at http://www.cbronline.com/article_news.asp?guid=A921B4EA-A489-4B5C-8053-423F46499767; CBR and CBRonline.com.
Nedos et al.; "LATTE: Location and Time Triggered Email"; pp. 1-14; located at https://www.cs.tcd.ie/publications/tech-reports/reports.04/TCD-CS-2004-32.pdf; Trinity College, Dublin, Ireland.
Parc Research; "Content Centric Networking"; bearing dates of 2002-2007; printed on Aug. 15, 2008; pp. 1-2; located at http://www.parc.xerox.com/research/projects/networking/contentcentric/default.html; Palo Alto Research Center Incorporated.
Pointofmail.com.; "Advanced Email Experience™"; bearing dates of 1999-2008 and printed on Aug. 15, 2008; p. 1; located at http://email.about.com/gi/dynamic/offsite.htm?zi=1/XJ&sdn=email&zu=http%3A%2F%2Fwww.readnotify.com%2F.
Roecker et al.; "Context-Dependent Email Notification Using Ambient Displays and Mobile Devices"; 2005; pp. 137-138; located at http://ieeexplore.ieee.org/iel5/10045/32238/01505288.pdf?tp=&isnumber=32238&arnumber=1505288; IEEE.
Techcrunch.com; "Seriosity to Fix Email Overload (or Not)" blog; bearing a date of Feb. 28, 2007 and printed on Aug. 13, 2008; pp. 1-12; located at http://www.techcrunch.com/2007/02/28/seriosity-to-fix-email-overload-or-not/all-comments/#comments.
Terdiman, Daniel; "A Cure for E-Mail Attention Disorder?"; CNET News.com; Feb. 28, 2007 and printed on Aug. 13, 2008; pp. 1-4; located at http://news.com.com/2100-1038_3-6162798.html; CNET Networks, Inc., a CBS Company.

(56) References Cited

OTHER PUBLICATIONS

Tschabitscher, Heinz; "BigString.com—Free Email Service"; About.com: Email; printed on Aug. 13, 2008; pp. 1-2; located at http://email.about.com/od/freeemailreviews/gr/bigstring_com.htm.

Tschabitscher, Heinz; "Confimax—Certified Email Service"; About.com: Email; printed on Aug. 13, 2008; pp. 1-2; located at http://email.about.com/cs/oepluginreviews/gr/confimax.htm.

Tschabitscher, Heinz; "DidTheyReadIt—Certified Email Service"; About.com: Email; printed on Aug. 13, 2008; pp. 1-2; located at http://email.about.com/od/windowsreturnreceipts/gr/didtheyreadit.htm.

Tschabitscher, Heinz; "E-mail Secure—Certified Email Service"; About.com: Email; printed on Aug. 13, 2008; pp. 1-2; located at http://email.about.com/od/windowsreturnreceipts/gr/e_mailsecure.htm.

Tschabitscher, Heinz; "Pointofmail 5.5—Certified Email Service"; About.com: Email; printed on Aug. 13, 2008; pp. 1-2; located at http://email.about.com/od/windowsreturnreceipts/gr/pointofmail.htm.

Tschabitscher, Heinz; "ReadNotify—Certified Email Service"; About.com: Email; printed on Aug. 13, 2008; pp. 1-2; located at http://email.about.com/od/windowsreturnreceipts/gr/readnotify.htm.

Twitter.com website located at http://twitter.com; [No document provided].

Westen et al.; "Neural Bases of Motivated Reasoning: An fMRI Study of Emotional Constraints on Partisan Political Judgment in the 2004 U.S. Presidential Election"; Journal of Cognitive Neuroscience; 2006; pp. 1947-1958; vol. 18; No. 11; Massachusetts Institute of Technology.

* cited by examiner

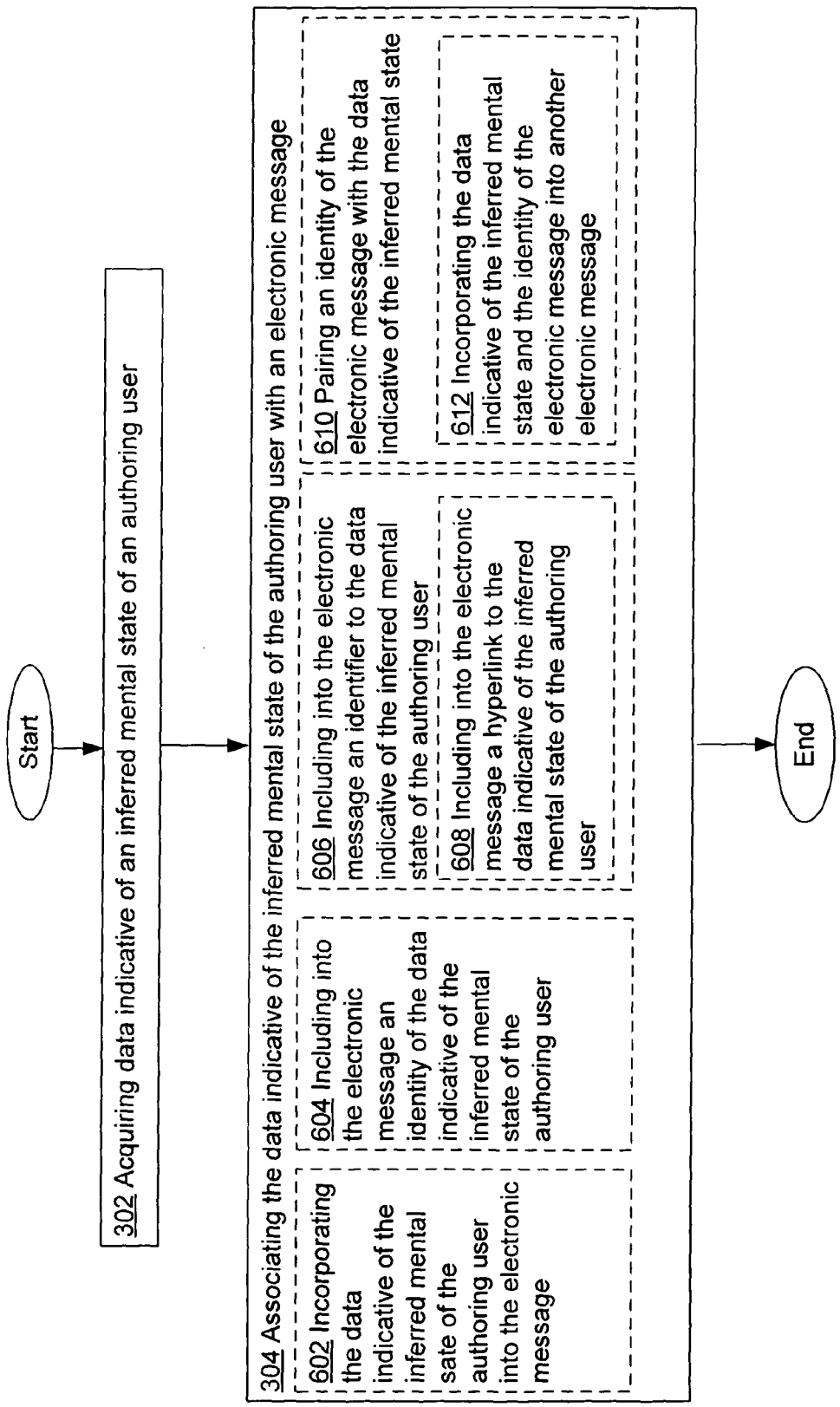

ACQUISITION AND ASSOCIATION OF DATA INDICATIVE OF AN INFERRED MENTAL STATE OF AN AUTHORING USER

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application is related to U.S. patent application Ser. No. 12/217,131, entitled ACQUISITION AND ASSOCIATION OF DATA INDICATIVE OF AN INFERRED MENTAL STATE OF AN AUTHORING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 30 Jun. 2008, which is currently co-pending, or is an application of which a currently co-pending application is entitled to the benefit of the filing date.

For purposes of the USPTO extra-statutory requirements, the present application is related to U.S. patent application Ser. No. 12/221,253, entitled ACQUISITION AND PARTICULAR ASSOCIATION OF DATA INDICATIVE OF AN INFERRED MENTAL STATE OF AN AUTHORING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 29 Jul. 2008, which is currently co-pending, or is an application of which a currently co-pending application is entitled to the benefit of the filing date.

For purposes of the USPTO extra-statutory requirements, the present application is related to U.S. patent application Ser. No. 12/221,197, entitled ACQUISITION AND PARTICULAR ASSOCIATION OF DATA INDICATIVE OF AN INFERRED MENTAL STATE OF AN AUTHORING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 30 Jul. 2008, which is currently co-pending, or is an application of which a currently co-pending application is entitled to the benefit of the filing date.

For purposes of the USPTO extra-statutory requirements, the present application is related to U.S. patent application Ser. No. 12/229,517, entitled ACQUISITION AND PARTICULAR ASSOCIATION OF INFERENCE DATA INDICATIVE OF AN INFERRED MENTAL STATE OF AN AUTHORING USER AND SOURCE IDENTITY DATA, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 21 Aug. 2008, which is currently co-pending, or is an application of which a currently co-pending application is entitled to the benefit of the filing date.

For purposes of the USPTO extra-statutory requirements, the present application is related to TICULAR ASSOCIATION OF INFERENCE DATA INDICATIVE OF AN INFERRED MENTAL STATE OF AN AUTHORING USER AND SOURCE IDENTITY DATA, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 29 Aug. 2008, which is currently co-pending, or is an application of which a currently co-pending application is entitled to the benefit of the filing date.

For purposes of the USPTO extra-statutory requirements, the present application is related to U.S. patent application Ser. No. 12/231,302, entitled ACQUISITION AND PARTICULAR ASSOCIATION OF INFERENCE DATA INDICATIVE OF AN INFERRED MENTAL STATE OF AN AUTHORING USER AND SOURCE IDENTITY DATA, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 29 Aug. 2008, which is currently co-pending, or is an application of which a currently co-pending application is entitled to the benefit of the filing date.

For purposes of the USPTO extra-statutory requirements, the present application is related to U.S. patent application Ser. No. 12/284,348, entitled ACQUISITION AND PARTICULAR ASSOCIATION OF INFERENCE DATA INDICATIVE OF INFERRED MENTAL STATES OF AUTHORING USERS, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 19 Sep. 2008, which is currently co-pending, or is an application of which a currently co-pending application is entitled to the benefit of the filing date.

For purposes of the USPTO extra-statutory requirements, the present application is related to U.S. patent application Ser. No. 12/284,710, entitled ACQUISITION AND PARTICULAR ASSOCIATION OF INFERENCE DATA INDICATIVE OF INFERRED MENTAL STATES OF AUTHORING USERS, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 23 Sep. 2008, which is currently co-pending, or is an application of which a currently co-pending application is entitled to the benefit of the filing date.

For purposes of the USPTO extra-statutory requirements, the present application is related to U.S. patent application Ser. No. 12/287,687, entitled ACQUISITION AND PRESENTATION OF DATA INDICATIVE OF AN EXTENT OF CONGRUENCE BETWEEN INFERRED MENTAL STATES OF AUTHORING USERS, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 10 Oct. 2008, which is currently co-pending, or is an application of which a currently co-pending application is entitled to the benefit of the filing date.

For purposes of the USPTO extra-statutory requirements, the present application is related to U.S. patent application Ser. No. 12/288,008, entitled ACQUISITION AND PRESENTATION OF DATA INDICATIVE OF AN EXTENT OF CONGRUENCE BETWEEN INFERRED MENTAL STATES OF AUTHORING USERS, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 14 Oct. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/154,686, entitled DETERMINATION OF EXTENT OF CONGRUITY BETWEEN OBSERVATION OF AUTHORING USER AND OBSERVATION OF RECEIVING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 23 May 2008 now U.S. Pat. No. 7,904,507, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/157,611, entitled DETERMINATION OF EXTENT OF CONGRUITY BETWEEN OBSERVATION OF AUTHORING USER AND OBSERVATION OF RECEIVING USER, naming Edward K. Y. Jung, Eric C. Leuthardt, Royce A. Levien, Robert W. Lord, Mark A. Malamud, John D. Rinaldo, Jr. and Lowell L. Wood, Jr. as inventors, filed 10 Jun. 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

A computationally implemented method includes, but is not limited to: acquiring data indicative of an inferred mental state of an authoring user; and associating the data indicative of the inferred mental state of the authoring user with an electronic message. In addition to the foregoing, other method aspects are described in the claims, drawings, and text forming a part of the present disclosure.

In one or more various aspects, related machines or articles of manufacture of systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

A computationally implemented system includes, but is not limited to: means for acquiring data indicative of an inferred mental state of an authoring user; and means for associating the data indicative of the inferred mental state of the authoring user with an electronic message. In addition to the foregoing, other system aspects are described in the claims, drawings, and text forming a part of the present disclosure.

A computationally implemented system includes, but is not limited to: circuitry for acquiring data indicative of an inferred mental state of an authoring user; and circuitry for associating the data indicative of the inferred mental state of the authoring user with an electronic message. In addition to the foregoing, other system aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 6 is a high-level logic flowchart of a process depicting alternate implementations of the association operation 304 of FIG. 3.

DETAILED DESCRIPTION

Figure 1:
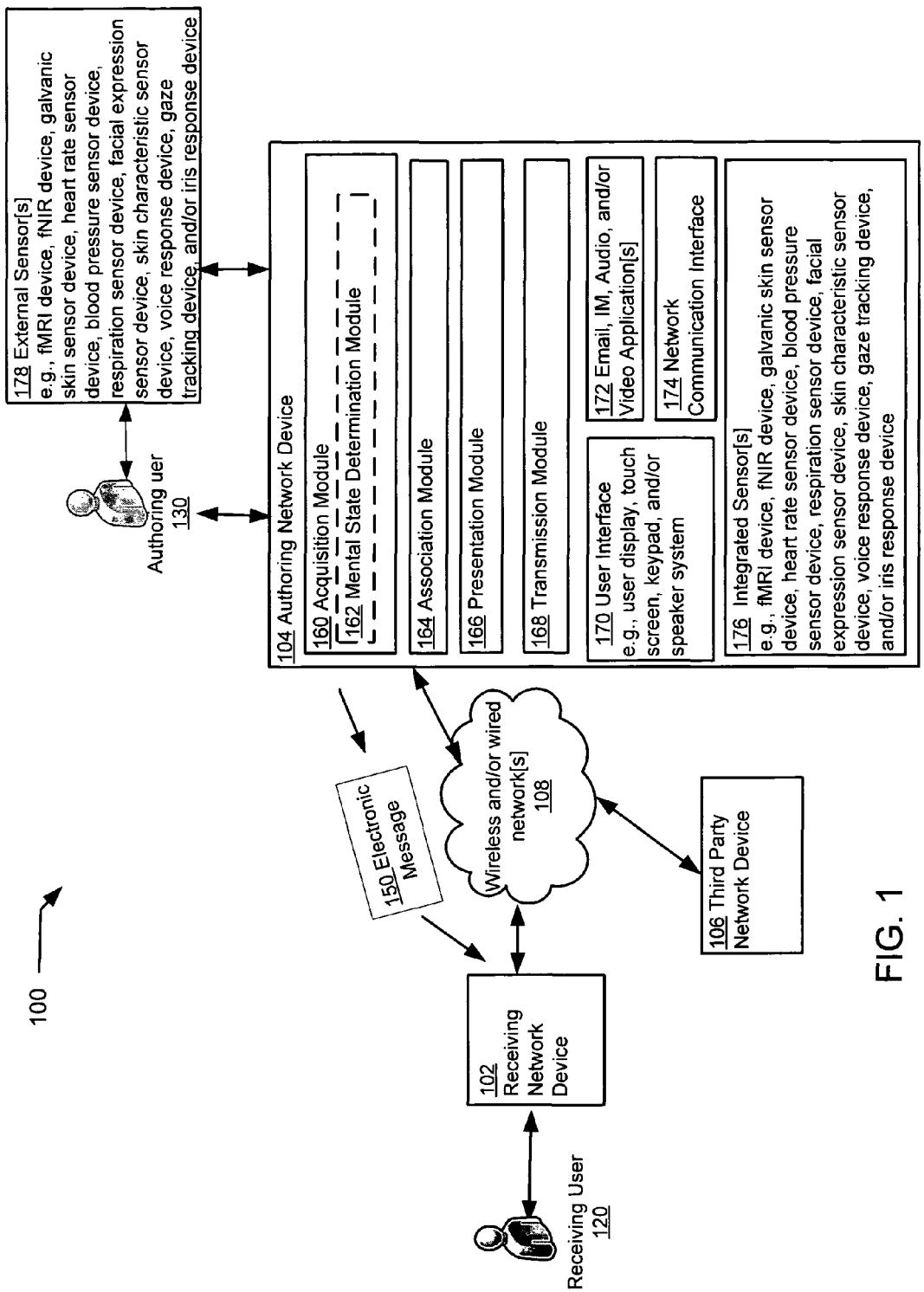
FIG. 1 shows a high-level block diagram of a network device operating in a network environment.

In the following detailed description, reference is, made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates an example environment in which one or more aspects of various embodiments may be implemented. In the illustrated environment, an exemplary system 100 may include at least an authoring network device 104 that may be used by an authoring user 130. In some implementations, the authoring network device 130 may be used in order to provide to a receiving user 120 (e.g., via a receiving network device 102) or to a third party network device 106 the context and/or tone of electronic messages (e.g., electronic message 150) authored and sent by the authoring user 130. Those skilled in the art will appreciate that although authoring user 130/receiving user 120 is depicted in the figures as an individual for sake of conceptual clarity, in some instances authoring user 130/receiving user 120 may be considered as examples of sequential users, unless context dictates otherwise.

In other words, the authoring network device 130 may be particularly configured to facilitate a receiving user 120 (and/or a third party participant via the third party network device 106) "get" the tone of electronic messages (e.g., email messages, instant messages (IM), audio messages, video messages, or other types of electronic messages) sent by the authoring user 130. In some instances, this may be accomplished by providing to the receiving user 120 data that may indicate a mental state of the authoring user 130 associated with an electronic message 150. Such a mental state may be a mental state that has been inferred based, at least in part, on one or more sensed or measured physical characteristics of the authoring user 130. That is, and as will be further described, a mental state of a subject (e.g., authoring user 130 or a receiving user 120) may be inferred based on, for example, the measured or detected physical characteristics of the subject. The term "physical characteristics" as used herein may refer to both external physical characteristics such as facial expression and iris characteristics and/or physiological characteristics such as blood oxygen or blood volume changes of a subject's brain.

For example, if the authoring user 130 composes and sends an electronic message 150 containing a humorous story to the receiving user 120 with the intent to lighten the mood of the receiving user 120, the authoring network device 104 may be advantageously designed to acquire data indicative of an inferred mental state of the authoring user 130 during or proximate to the composition of the electronic message 150 by the authoring user 130. After acquiring such data, the data may then be associated with the electronic message 150 and transmitted to the receiving user 120 with the electronic message 150 or by other means to the receiving user 120. In doing so, the receiving user 120 may be made aware of whether the receiving user 120 is misunderstanding the tone and/or meaning of the electronic message (e.g., the receiving user 120 becomes mistakenly distressed by the electronic message because the receiving user 120 misunderstands the tone of the message) when reading the electronic message 150.

In some instances, this may be accomplished by comparing the inferred mental state of the authoring user 130 during or proximate to the composition or drafting of the electronic message 150 by the authoring user 130, and the inferred mental state of the receiving user 120 during or proximate to the presentation of the electronic message 150 to the receiving user 120. According to some embodiments, the mental states of users (e.g., receiving user 120 and/or authoring user 130) may be inferred by observing one or more physical characteristics of the users. The inferred mental states of the receiving user 120 and the authoring user 130 may be compared in some instances at the receiving network device 102 in order determine congruity between the inferred mental states of the receiving and authoring users 120 and 130. Alternatively, such comparison and congruity determination may be made at the third party network device 106. These and other aspects of various embodiments will be described in greater detail herein.

Referring back to FIG. 1, the authoring network device 104 may communicate with the receiving network device 102, and in some instances, may also communicate with a third party network device 106 via a wireless and/or wired network [s] 108. The authoring network device 104 may be any type of computing and/or communication device such as a personal computer (PC), a laptop computer, a personal digital assistant (PDA), a cellular telephone, a blackberry, and so forth.

The authoring network device 104 may include various components including, for example, an acquisition module 160 for acquiring data indicative of an inferred mental state of the authoring user 130. In some instances, the acquisition of the data may include observing one or more physical characteristics of the authoring user 130 by employing one or more integrated sensors 176 and/or one or more external sensors 178 to measure the physical characteristics of the authoring user 130. In some implementations, the acquisition module 160 may include a mental state determination module 162 for determining an inferred mental state of the authoring user 130 based, at least in part, on the observation of one or more physical characteristics of the authoring user 130. Alternatively, the inferred mental state of the authoring user 130 may be externally determined in some alternative implementations (e.g., to be performed by a mental state determination module 162 included in the third party network device 106). In some instances, the observation of the one or more physical characteristics of the authoring user 130 using the one or more sensors 176/178 may be performed during or proximate to the composition by the authoring user 130 of the electronic message 150.

In addition to the acquisition module 160, the authoring network device 130 may also include an association module 164 for associating the data indicative of the inferred mental state of the authoring user 130 to the electronic message 150. In various embodiments, the authoring network device 104 may further include a presentation module 166 and/or a transmission module 168. In brief, and as will be further described, the presentation module 166 may be for presenting the data indicative of the inferred mental state of the authoring user 130 while the transmission module 168 may be employed in order to transmit the data indicative of the inferred mental state of the authoring user 130. Such data may be used by, for example, the receiving network device 102 and/or third party network device 106 to determine an extent of congruity between the inferred mental state associated with the authoring user 130 (e.g., during or proximate to the composition of an electronic message 150 by the authoring user 130) and the inferred mental state of the receiving user 120 (e.g., during or proximate to the presentation of the electronic message 150 to the receiving user 120). The determination of the congruity of the inferred mental states of the authoring user 130 and the receiving user 120 may indicate as to whether the authoring user 130 and the receiving user 120 are, in effect, "on the same page" and/or "gets" the tone and intent of the message, which in some instances might be as a result of an exchange of communication (e.g., transmission and presentation of electronic message 150).

For example, suppose the intent of the authoring user 130 is to lighten the mood of the receiving user 120 by sending to the receiver user 120 an electronic message 150 containing a joke. A determination may be made as to the congruity of the inferred mental state (e.g., presumably happy) of the authoring user 130 during or proximate to the composition of the electronic message 150 by the authoring user 130 and the inferred mental state (e.g., hopefully happy) of the receiving user 120 during or proximate to the presentation of the electronic message 150 to the receiving user 120. By determining the congruity of the mental states of the authoring user 130 and the receiving user 120 (as they relate to the electronic message 150), a determination may be made as to whether the intent of the electronic message 150 (e.g., to lighten the mood of receiving user 120) was successful.

Note that in some situations the mental states of the authoring user 130 and the receiving user 120 may not need to be in congruence with each other in order to conclude that the receiving user 120 "got" the tone and meaning of the electronic message 150. That is, in some cases, the desired outcome or desired intent of the electronic message 150 may not result in the congruence of the mental states of the authoring user 130 and the receiving user 120 when the receiving user 120 correctly understands the tone and meaning of the electronic message 150. For instance, if the intent of the authoring user 130 is to anger the receiving user 120 by including, for example, a sarcastic remark into the electronic message 150, then the mental state (e.g., state of disapproval) of the authoring user 130 may not necessarily be in congruence with the mental state (e.g., state of anger) of the receiving user 120 even though the receiving user 120 may have "got" the tone and meaning of the electronic message 150 when the electronic message 150 was presented to the receiving user 120.

The authoring network device 104 may additionally include a user interface 170, an email, instant message (IM), audio, and/or video application[s] 172, a network communication interface 174, and/or one or more integrated sensors 176. In some implementations, the user interface 170 may, in fact, be one or more interfaces such as a user display, a touch screen, a keypad, a speaker system, and so forth for interacting with the authoring user 130. In order to present the data indicative of the inferred mental state of the authoring user 130, the presentation module 166 in some implementations may present such data via the email, IM, audio, and/or video application[s] 172 (an audio application may be, in some implementations, a voice over internet protocol application or simply "VoIP"). The network communication interface 174 may be employed to interface with, for example, a wireless and/or a wired network 108. As described above, the authoring network device may further include one or more integrated sensors 176 for monitoring or measuring one or more physical characteristics of the authoring user 130. In some implementations or the same implementations, the authoring network device 104 may employ one or more external sensors 178 to monitor or measure one or more physical characteristics of the authoring user 130.

Examples of sensors 176/178 that may be employed by the authoring network device 104 include, for example, devices that can measure brain activities such as a functional near-infrared imaging (fNIR) device, a functional magnetic resonance imaging (fMRI) device, a magnetoencephalography (MEG) device, an electroencephalography (EEG) device, and/or a positron emission topography device. These devices may measure a variety of physiological parameters that may be processed in order to determine an inferred mental state of a subject (e.g., authoring user 130). Other types of sensors such as those that measure other types of physical characteristics may be employed as sensor[s] 176/178. For example, in some implementations, the sensor[s] 176/178 may include an iris response device, a gaze tracking device, a skin response device (e.g., galvanic skin sensor), and/or a voice response device. In some alternative implementations, the authoring network device 104 may be wirelessly (e.g., wireless personal area network (WPAN), wireless local area network (WLAN), and so forth) and/or wired connected to one or more external sensors 178.

Data obtained from observations made with one or more such sensors 176/178 may be used by, for example, the mental state determination module 162 in order to determine an inferred mental state of the authoring user 130 including, for example, preference, trust, fear, happiness, surprise, inattention, arousal, impatience, confusion, distraction, overall mental activity, alertness, acuity, fear, pain, distress, anger, deception, fairness or unfairness, frustration, approval and disapproval, degree of attention, memory usage—both short and long term, of the authoring user 130. For example, data obtained from one or more sensors 176/178 that includes an fNIR device may indicate that a subject (e.g., authoring user 130) is in at least one of a state of anger, a state of distress, or a state of pain. Data obtained from such sensors 176/178 as well as other types of sensors may also indicate that a subject is in a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, a state of acuity, or other types of mental states.

Figure 2:
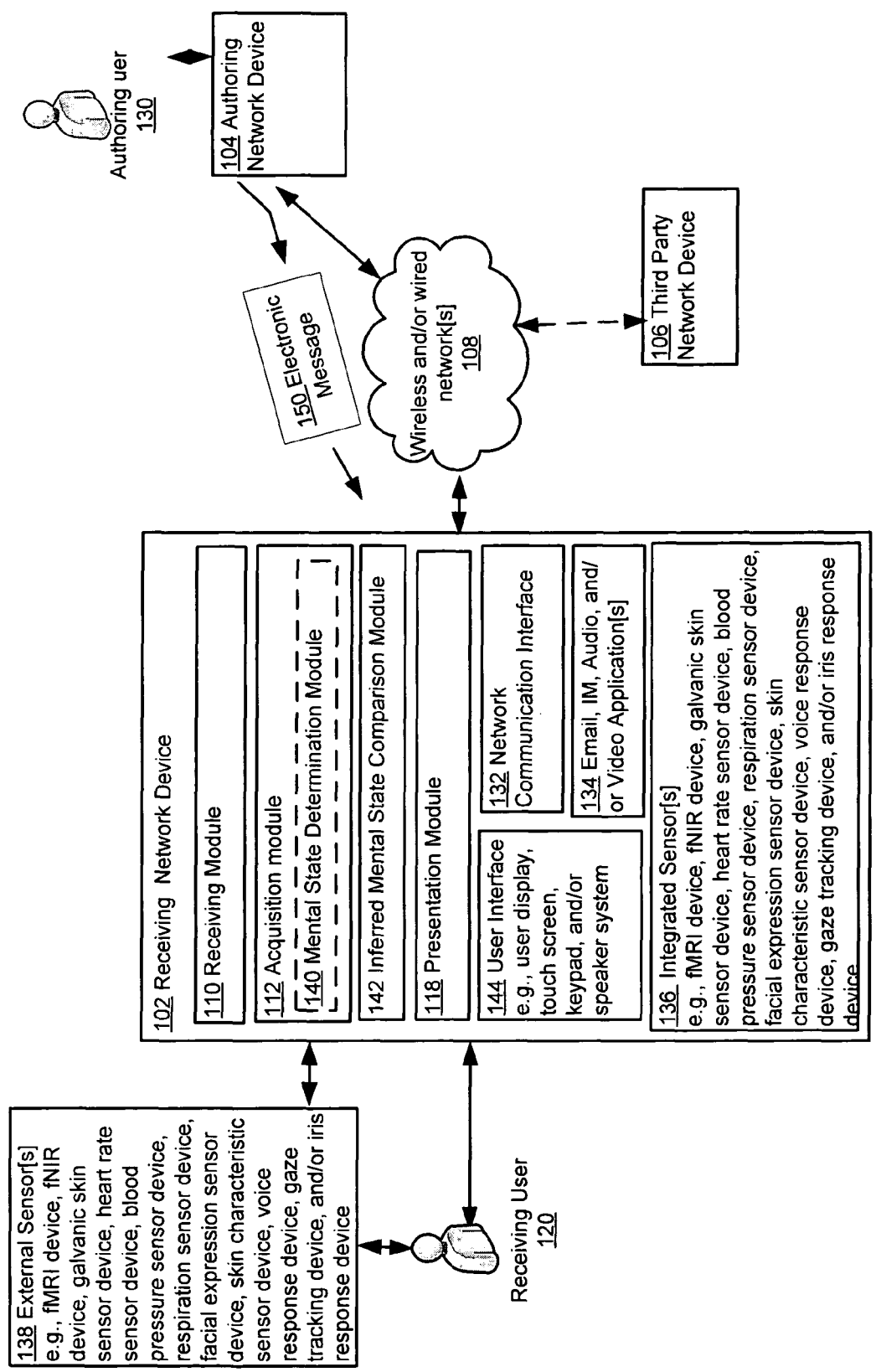
FIG. 2 shows another perspective of the network environment of FIG. 1.

In order to appreciate various aspects of the authoring network device 104, the following illustrative example is provided in which the authoring network device 104 communicates with one or more network devices including receiving network device 102. In this example, the authoring user 130 using the authoring network device 104 may initially compose an electronic message 150, which may be subsequently transmitted to the receiving network device 102 (and/or third party network device 106). Turning now to FIG. 2, which is another perspective of the exemplary environment depicted in FIG. 1. More particularly, FIG. 2 depicts the receiving network device 104 having some of the same components as the authoring network device 104 as illustrated in FIG. 1. For instance, and similar to the authoring network device 104, the receiving network device 102 includes an acquisition module 112, which may further include a mental state determination module 140, a presentation module 118, a user interface 144, a network communication interface 132, an email, IM, audio, and/or video applications 134, and one or more external and/or integrated sensors 136/138. These components may serve functions similar to those of their counterparts in the authoring networking device 104.

In addition to these components, the receiving network device 102 may also include a receiving module 110 for receiving data indicative of one or more inferred mental states of the authoring user 130. The received data may be in at least one of two different forms. In the first form, the received data is sensor provided data of one or more physical characteristics of the authoring user 130 that has been collected from one or more sensors 176/178. In some implementations, such data may be further processed by the receiving network device 102 in order to derive one or more inferred mental states of the authoring user 130. In the second form, the received data may be processed data (e.g., as processed by the authoring network device 104 via the mental state determination module 162) as a result of processing the "raw" data provided by one or more sensors 176/178. In some embodiments, the processed data may directly indicate one or more inferred mental states of the authoring user 130.

The receiving network device 102 may further include an inferred mental state comparison module 142. The inferred mental state comparison module 142 may be employed in order to compare an inferred mental state of the authoring user 130 with an inferred mental state of the receiving user 120. Such a comparison may be used in order to determine the congruity between the inferred mental states of the authoring user 130 and the receiving user 120 during or proximate to an exchange of, for example, the electronic message 150.

The electronic message 150 to be sent to and received by the receiving network device 102 may be in a form of an email message, an IM message, an audio message, a video message, or another type of electronic message that may be sent by the authoring user 130 via the authoring network device 104. The receiving network device 102 may receive the electronic message 150 through the network communication interface 132. Along with the electronic message 150, the receiving network device 102 may receive from the authoring network device 104, via the receiving module 110, data indicative of an inferred mental state of the authoring user 130, which may be included in the electronic message 150 or in another electronic message. After receiving the electronic message 150, the electronic message 150 may be presented to the receiving user 120 by the presentation module 118 via the email, IM, audio, and/or video application[s] 134 and through the user interface 144.

During or proximate to the presentation of the electronic message 150 to the receiving user 120 (e.g., via the presentation module 118), the receiving network device 102, which may be endowed with one or more sensors 136/138, may observe one or more physical characteristics of the receiving user 120. Based on the observation of the one or more physical characteristics of the receiving user 120, the receiving network device 102, and more particularly, the mental state determination module 140, may infer one or more mental states of the receiving user 120. The mental state determination module 140 (as well as the mental state determination module 162 of the authoring network device 104 of FIG. 1) may employ different techniques in order to infer one or more mental states from observed physical characteristics of a subject (e.g., authoring user 130 or receiving user 120). In some implementations, this may mean associating particular physical characteristics or patterns of physical characteristics to one or more mental states (i.e., inferred mental states).

For example, if the one or more sensors 136/138 depicted in FIG. 2 include an fMRI device, then the fMRI device may be used in order to scan the brain of the subject (e.g., receiving user 120) during or proximate to the presentation to the receiving user 120 of the electronic message 150. As a result of the functional magnetic resonance imaging (fMRI) procedure performed using the fMRI device; the fMRI device may provide a profile or a pattern of brain activities (e.g., blood oxygen and/or blood volume changes of the brain) of the receiving user 120 during or proximate to the presentation of the electronic message 150 to the receiving user 120. The determined "brain activity pattern" may then be compared to brain activity patterns that may have been previously recorded and stored in a database or library. In some implementations, such a database or library may include information relative to the subject (e.g., in this case, the receiving user 120) including, for example, log of raw sensor data or data of mappings between sensor data and known or inferred mental states that may be used in order to "calibrate" data received from the one or more sensors 136/138. Alternatively, a model may be employed that associates different patterns of brain activities with different mental states. Such a model may be used in conjunction with data received from other types of sensors (e.g., those types of sensors that do not measure brain activities) in order to associate, for example, a pattern of brain activity with one or more mental states.

Such a database or library may contain numerous brain activity patterns that may have been obtained by sampling a number of people from the general population, having, for example, similar metrics (e.g., age, gender, race, education, and so forth) as the subject (e.g., receiving user 120). By asking each person what they felt (e.g., mental state) at the time when their brain activity pattern was recorded, or by using, for example, some other established testing procedures, each brain activity pattern stored in the library or database may be associated with one or more mental states.

As a result, by comparing the determined brain activity pattern of the receiving user 120 with the brain activity patterns stored in the database or library, one or more mental states may be inferred from the observed physical characteristics of the receiving user. Note that an inferred mental state of the authoring user 130 during or proximate to the composition of the electronic message 150 by the authoring user 130 may be similarly determined using one or more sensors 176/178.

In any event, an inferred mental state or states of the receiving user 120 during or proximate to the presentation of the electronic message 150 may be compared with, via the inferred mental state comparison module 142, an inferred mental state or states of the authoring user 120 during or proximate to the composition of the electronic message 150. In some implementations, the inferred mental state or states of the authoring user 120 may be provided by the authoring network device 104 to the receiving network device 102 via the electronic message 150 or via some other electronic message.

Alternatively, instead of providing data that directly identifies the mental state or states of the authoring user 130; the authoring networking device 104 may provide to the receiving network device 102 "raw" or unprocessed data that was obtained using sensors 176/178 of one or more physical characteristics of the authoring user 130. For example, in some implementations, the authoring network device 104 may provide to the receiving network device 102 data indicating the physical characteristics (e.g., brain activity) observed or measured by a sensor 176/178 (e.g., fNIR device) rather than an inferred mental state determined by the mental state determination module 162 of the authoring network device 104. In this particular implementation, the receiving network device 102 (e.g., using an mental state determination module 140 or similar such module disposed in the receiving module 110) may then process the raw data obtained from the authoring network device 104 to determine an inferred mental state or states of the authoring user 130 during or proximate to the composition of the electronic message 150.

The receiving module 110 of the receiving network device 102 may initially receive the electronic message 150 transmitted by the authoring network device 104 as well as data indicative of an inferred mental state (e.g., raw data provided by sensors 176/178 or data that indicates or directly identifies the inferred mental state or states of the authoring user 130 as provided by, for example, the mental state determination module 162) of the authoring user 130. In particular, the receiving module 110 in some implementation may employ the network communication interface 132 and the email, IM, audio, and/or video applications 134 in order to receive and process the electronic message 150. In some instances, the receiving module 110 may also receive and process data indicative of the inferred mental state of the authoring user 130.

If the data indicative of the inferred mental state of the authoring user 130 that is received is, in fact, in the form of raw data from sensors 176/178 instead of in the form of data that directly identifies an inferred mental state of the authoring user 130, then the received results may be processed by, for example, a mental state determination module 140 or similar such module, in order to obtain an inferred mental state of the authoring user 130 during or proximate to the composition of the electronic message 150. The term "proximate" as used herein may refer to, in some instances, partly during, immediately subsequent, or immediately preceding the composition of the electronic message 150.

After receiving the electronic message 150 from the authoring network device 104, the receiving network device 102 may present or display the electronic message 150 to the receiving user 120 via the user interface 144. During or proximate to the presentation of the electronic message 150 to the receiving user 120, the acquisition module 112 using one or more sensors 136/138 may make an observation of one or more physical characteristics of the receiving user 120. In some implementations, and as previously described, the mental state determination module 140 may determine an inferred mental state for the receiving user 120 based, at least in part, on the results of the observation of the one or more physical characteristic of the receiving user 120.

In some implementations, the observation of one or more of the physical characteristics of the receiving user 120 may be made by using one or more sensors 136/138. For example, in some embodiments, a single or multiple sensors 136/138 such as a combination of a galvanic skin sensor, an iris response device, a gaze tracking device, and/or a voice response device may be used in order to observe various physical characteristics of the receiving user 120 when the electronic message 150 is being presented to the receiving user 120. Based on the observations made by the multiple sensors 136/138, the sensors 136/138 may output raw data indicating the physical characteristics of the receiving user 120. Such raw data may include, for example, galvanic skin response data provided by a galvanic skin sensor and a gaze tracking (e.g., eye movement) data obtained from a gaze tracking device. The raw data may then be used by the mental state determination module 140 in order to infer one or more mental states for the receiving user 120.

The comparison module 114, in some instances, may then compare the results of the observation (e.g., inferred mental state during or proximate to the composition of the electronic message 150) of the authoring user 130 with the results of the observation (e.g., inferred mental state during or proximate to the presentation of the electronic message 150) of the receiving user 120. Based on this comparison, the presentation module 118 may present an extent of congruity between the result of the observation of the authoring user 130 and the result of the observation of the receiving user 120 to the receiving user 120 and/or to the third party network device 106. The extent of congruity may facilitate in determining whether the receiving user 120 is "getting" the tone and meaning of the electronic message 150 sent by the authoring user 130.

Referring back to FIG. 1, the various components (e.g., acquisition module 160, mental state determination module 162, association module 164, presentation module 166, transmission module 168, and so forth) included with the authoring network device 104 may be embodied by hardware, software and/or firmware in one or more machines or articles of manufacture. For example, in some implementations the acquisition module 160, the mental state determination module 162, the association module 164, the presentation module 166, and the transmission module 168 may be implemented with a processor (e.g., microprocessor, controller, and so forth) executing computer readable instructions (e.g., computer program product) stored in a storage medium (e.g., volatile or non-volatile memory) such as a non-transitory storage medium. Alternatively, hardware such as application specific integrated circuit (ASIC) may be employed in order to implement such modules in some alternative implementations.

Figure 3:
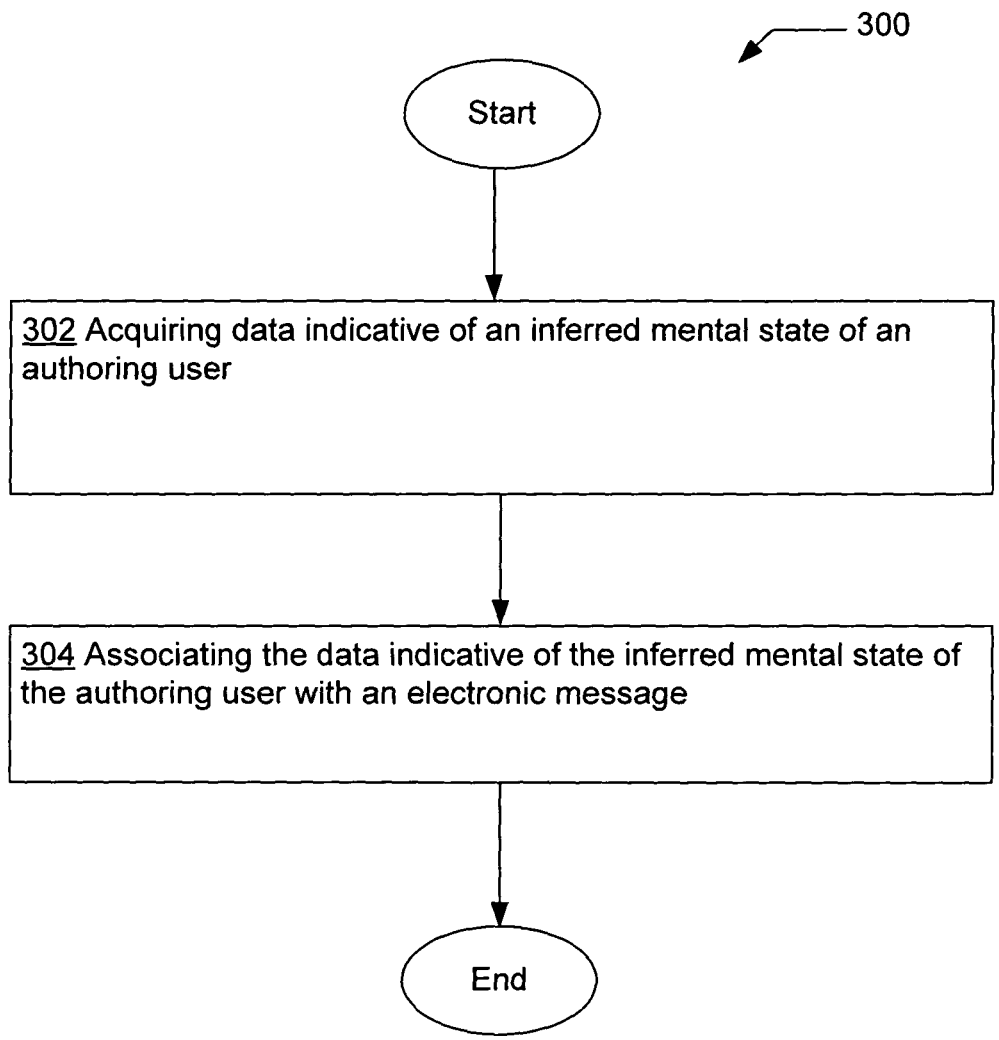
FIG. 3 is a high-level logic flowchart of a process.

FIG. 3 illustrates an operational flow 300 representing example operations related to acquisition and association of data indicative of an inferred mental state of an authoring user. In FIG. 3 and in the following figures that include various examples of operational flows, discussions and explanations may be provided with respect to the above-described exemplary environment of FIGS. 1 and 2, and/or with respect to other examples and contexts. However, it should be understood that the operational flows may be executed in a number of other environments and contexts, and/or in modified versions of FIGS. 1 and 2. Also, although the various operational flows are presented in the sequence(s) illustrated, it should be understood that the various operations may be performed in other orders than those which are illustrated, or may be performed concurrently.

Further, in FIG. 3 and in following figures, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

In any event, after a start operation, the operational flow 300 may move to an acquisition operation 302, where acquiring data indicative of an inferred mental state of an authoring user may be executed by, for example, the acquisition module 160 of FIG. 1. For example, such data may be acquired, at least in part, by the authoring network device 104 of FIG. 1 using the acquisition module 160 and employing one or more sensors 176/168 to sense (e.g., measure, scan, or detect) one or more physical characteristics (e.g., brain activities) of the authoring user 130. The data to be acquired may be in the form of raw or unprocessed data collected from the one or more sensors 176/178 (e.g., an fNIR device and/or fMRI device), which when processed, may provide data that identifies one or more inferred mental states (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) of the authoring user 130. Alternatively, the data to be acquired may be in the form of data (e.g., as provided by the mental state determination module 162) that may directly identify one or more inferred mental states of the authoring user 130. The one or more inferred mental states of the authoring user 130 to be identified by the acquired data may include at least one of, for example, a state of anger, a state of distress, a state of pain, a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, a state of acuity, and/or other types of mental states.

The operational flow 300 may then move to an association operation 304 where associating the data indicative of the inferred mental state of the authoring user with an electronic message may be executed by, for example, the association module 164 of FIG. 1. For example, in some implementations, the data (e.g., as provided by one or more sensors 176/178 and/or by mental state determination module 162) indicative of the inferred mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) of the authoring user 130 may be associated by the association module 164 with an electronic message 150 (e.g., an email message) by incorporating the data indicative of the inferred mental state of the authoring user 130 into the electronic message 150.

In some alternative implementations, the association operation 304 may involve including, via the association module 164, an identity (e.g., in the form of symbolic, numeric, and/or textual representation) of the data indicative of the inferred mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, state of acuity, and/or other types of mental states) of the authoring user 130 into the electronic message 150 (e.g., email message). In still other implementations, the acquisition operation 304 may involve adding into the electronic message 150 by the association module 164 a link to the data indicative of the inferred mental state (e.g., state of anger, state of distress, state of pain, state of frustration, state of approval or disapproval, state of trust, state of fear, and/or state of happiness, state of surprise, state of inattention, state of arousal, state of impatience, state of confusion, state of distraction, state of overall mental activity, state of alertness, state of acuity, and/or other types of mental states) of the authoring user 130 where the link, in some implementations, may be a hyperlink. The electronic message 150 (e.g., transmitted via the user interface 170) that the data indicative of the inferred mental state (e.g., inferred state of happiness) of the authoring user 150 may be associated with may be, in various implementations, an email message, an IM message, an audio message, a video message, and/or another type of electronic message.

Figure 4:
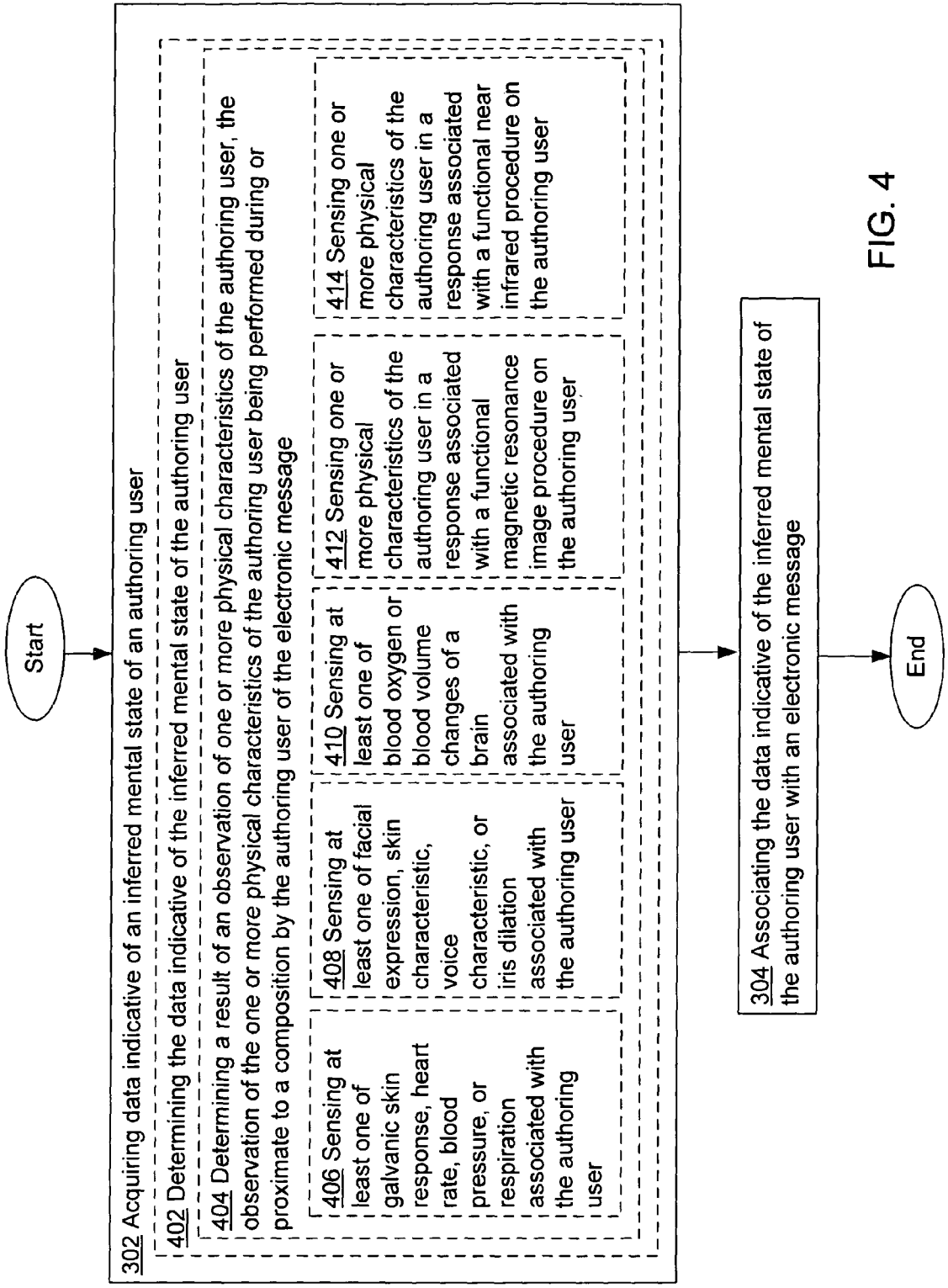
FIG. 4 is a high-level logic flowchart of a process depicting alternate implementations of the acquisition operation 302 of FIG. 3.

FIG. 4 illustrates various embodiments of the example acquisition operation 302 of FIG. 3. In particular, FIG. 4 illustrates example embodiments where the acquisition operation 302 includes at least one addition operation 402. For example, in some embodiments, the acquisition operation 302 may include a determination operation 402 where determining the data indicative of the inferred mental state of the authoring user may be executed. For instance, in some implementations, this may entail, the acquisition module 164 of the authoring network device 104 of FIG. 1 determining the data (e.g., "raw" data) provided by one or more sensors 176/178 or data that may directly identify an inferred mental state (e.g., state of anger, state of distress, state of pain, state of frustration, state of approval or disapproval, state of trust, state of fear, and/or state of happiness, state of surprise, state of inattention, state of arousal, state of impatience, state of confusion, state of distraction, state of overall mental activity, state of alertness, state of acuity, and/or other types of mental states) as provided by mental state determination module 162 indicative of the inferred mental state (e.g., state of anger) of the authoring user 130. In some implementations, the determination operation 402 may further include additional one or more operations.

For example, in some embodiments, the determination operation 402 may include another or second determination operation 404 for determining a result of an observation of one or more physical characteristics of the authoring user, the observation of the one or more physical characteristics of the authoring user being performed during or proximate to a composition by the authoring user of the electronic message. For instance, in some implementations, the determination operation 404 may include determining by the acquisition module 160 of the authoring network device 104 a result of an observation (e.g., based on data provided by one or more sensors 176/178 such as a fNIR and/or a fMRI device) of one or more physical characteristics (e.g., blood oxygen and/or blood volume changes of the brain) of the authoring user 130, the observation of the one or more physical characteristics of the authoring user 130 being performed during or proximate to a composition (e.g., drafting) by the authoring user 130 of the electronic message 150 (e.g., email).

In various embodiments, the determination operation 404 of FIG. 4 may include one or more additional operations. For example, in some embodiments, the determination operation 404 may include a sensing operation 406 for sensing at least one of galvanic skin response, heart rate, blood pressure, or respiration associated with the authoring user. For instance, in some implementations, sensing operation 406 may include the acquisition module 160 of the authoring network device 104 sensing (e.g., by employing one or more sensors 176/178 including, for example, a galvanic skin sensor, heart rate monitor, blood pressure monitor, and/or respiratory monitoring device) at least one of galvanic skin response, heart rate, blood pressure, or respiration associated with the authoring user 130.

In the same or alternative embodiments, the determination operation 404 may include another sensing operation 408 for sensing at least one of facial expression, skin characteristic, voice characteristic, eye movement, or iris dilation associated with the authoring user. For instance, in some implementations, the sensing operation 408 may include the authoring network device 104 of FIG. 1 sensing (e.g., via the acquisition module 160) at least one of facial expression, skin characteristic, voice characteristic, or iris dilation (e.g., as detected by one or more sensors 176/178, wherein the one or more sensors 176/178 includes an image capture device for capturing facial expressions, a galvanic skin response device, an audio capturing device for detecting voice characteristics, and/or an iris tracking device for detecting iris dilation) associated with the authoring user 130.

In the same or alternative embodiments, the determination operation 404 may include another sensing operation 410 for sensing at least one of blood oxygen or blood volume changes of a brain associated with the authoring user. For example, the sensing operation 410 may include the authoring network device 104 sensing (e.g., via the acquisition module 160) at least one of blood oxygen or blood volume changes of a brain (e.g., as measured by one or more sensors 176/178 such as an fNIR device and/or fMRI device) associated with the authoring user 130.

In the same or alternative embodiments, the determination operation 404 may include another sensing operation 412 for sensing one or more physical characteristics of the authoring user in a response associated with a functional magnetic resonance image procedure on the authoring user. For instance, in some implementations, the sensing operation 412 may include the authoring network device 104 of FIG. 1 sensing (e.g., via the acquisition module 160) one or more physical characteristics (e.g., blood oxygen and/or blood volume changes) of a brain of the authoring user 130 in a response associated with a functional magnetic resonance image procedure (e.g., as performed by one or more sensors 176/178 including one or more fMRI devices) on the authoring user 130.

In the same or alternative embodiments, the determination operation 404 may include another sensing operation 414 for sensing one or more physical characteristics of the authoring user in a response associated with a functional near infrared procedure on the authoring user. For instance, in some implementations, the sensing operation 414 may include the authoring network device 104 sensing (e.g., via the acquisition module 160) one or more physical characteristics (e.g., blood oxygen or blood volume changes of a brain) of the authoring user 130 in a response associated with a functional near infrared procedure (e.g., as performed by one or more sensors 176/178 including one or more fNIR devices) on the authoring user 130.

Figure 5:
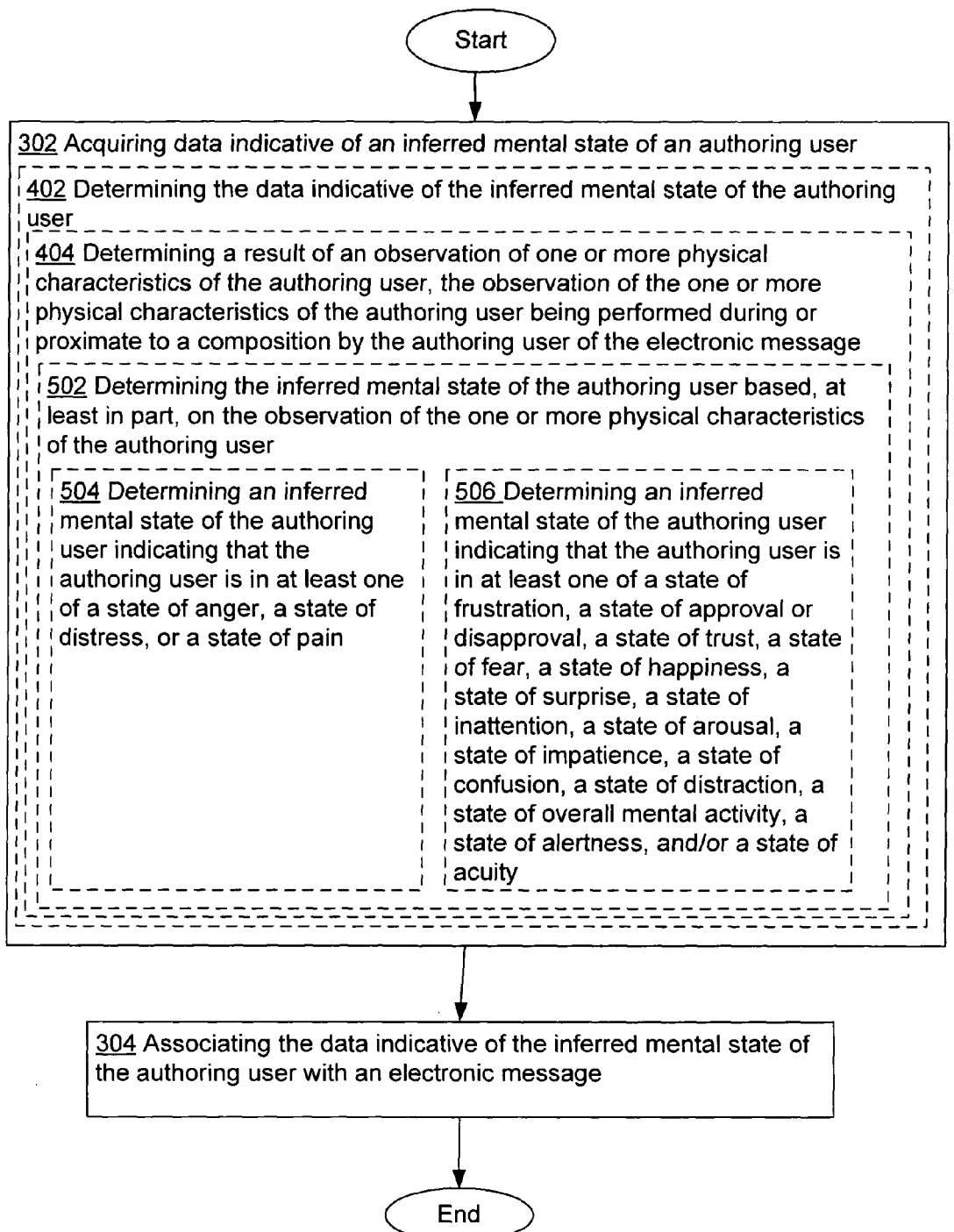
FIG. 5 is a high-level logic flowchart of a process depicting alternate implementations of the determination operation 404 of FIG. 4.

FIG. 5 illustrates certain embodiments of operation 404 of FIG. 4. In particular, FIG. 5 illustrates embodiments where operation 404 includes one or more additional and/or alternative operations to those operations (e.g., operations 406, 408, 410, 412, and 414) depicted in FIG. 4 for operation 404. For example, in some embodiments, the operation 404 may include another or a third determination operation 502 for inferring a mental state of the authoring user based, at least in part, on an observation of one or more physical characteristics of the authoring user. For instance, in some implementations, the determination operation 502 may include the authoring network device 104 of FIG. 1 inferring (e.g., via the mental state determination module 162) a mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) of the authoring user 130 based, at least in part, on an observation (e.g., using one or more sensors 176/178 including one or more galvanic skin sensors) physical characteristics (e.g., galvanic skin response) of the authoring user 130.

In various embodiments, operation 502 may further include a determination operation 504 and/or a determination operation 506. For example, in some embodiments, operation 502 may include the determination operation 504 for inferring a mental state of the authoring user indicating that the authoring user is in at least one of a state of anger, a state of distress, or a state of pain. For instance, in some implementations, the determination operation 504 may include the authoring network device 130 inferring (e.g., via the mental state determination module 162) a mental state of the authoring user 130 indicating that the authoring user 130 is in at least one of a state of anger, a state of distress, or a state of pain (e.g., based on data provided by one or more sensors 176/178 including, for example, an iris response device, a gaze tracking device, a skin response device such as a galvanic skin sensor, and/or a voice response device).

In the same or alternative embodiments, operation 502 may further include another determination operation 506 for inferring a mental state of the authoring user indicating that the authoring user is in at least one of a state of frustration, a state of approval or disapproval, a state of trust, a state of fear, a state of happiness, a state of surprise, a state of inattention, a state of arousal, a state of impatience, a state of confusion, a state of distraction, a state of overall mental activity, a state of alertness, or a state of acuity. For instance, in some implementations, operation 506 may include the authoring network device 130 inferring (e.g., via the mental state determination module 162) a mental state of the authoring user 130 indicating that the authoring user 130 is in at least one of a state of frustration, a state of approval or disapproval, a state of trust, a state of fear, or a state of happiness, a state of surprise, a state of inattention, a state of arousal, a state of impatience, a state of confusion, a state of distraction, a state of overall mental activity, a state of alertness, or a state of acuity (e.g., based, at least in part, on data provided by one or more sensors 176/178 including, for example, an fNIR device and/or an fMRI device).

FIG. 6 illustrates various embodiments of the association operation 304 of FIG. 3. More particularly, FIG. 6 illustrates example embodiments where the association operation 304 may include one or more additional and/or alternative operations. For example, in some embodiments, the association operation 304 may include an incorporation operation 602 for incorporating the data indicative of the inferred mental sate of the authoring user into the electronic message. For instance, in some implementations, incorporation operation 602 may include the authoring network device 104 of FIG. 1 incorporating (e.g., via the association module 164) the data (e.g., as provided by one or more sensors 176/178 and/or by mental state determination module 162) indicative of the inferred mental sate (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) of the authoring user 130 into the electronic message 150 (e.g., an IM message).

In the same or alternative embodiments, the association operation 304 may also include an inclusion operation 604 for including into the electronic message an identity of the data indicative of the inferred mental state of the authoring user. For instance, in some implantations, the inclusion operation 604 may include the authoring network device 104 including (e.g., via the association module 164) into the electronic message (e.g., a voice or audio message) an identity (e.g., a symbolic, numeric, and/or textural representation) of the data (e.g., as provided by one or more sensors 176/178 and/or by mental state determination module 162) indicative of the inferred mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) of the authoring user 130.

In the same or alternative embodiments, the association operation 304 may include another inclusion operation 606 for including into the electronic message an identifier to the data indicative of the inferred mental state of the authoring user. For example, in some implantations, the inclusion operation 606 may include the authoring network device 104 including (e.g., as executed by the association module 164) into the electronic message 150 (e.g., an email message), an identifier (e.g., pointer to a network address, a link (e.g., hyperlink), a pointer to computer storage, etc.) to the data (e.g., as provided by one or more sensors 176/178 and/or by mental state determination module 162) indicative of the inferred mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) of the authoring user 130.

In some embodiments, the inclusion operation 606 may further include an operation 608 for including into the electronic message a hyperlink to the data indicative of the inferred mental state of the authoring user. For instance, in some implementations, the operation 608 may include the authoring network device 104 of FIG. 1 including (e.g., via the association module 164) into the electronic message (e.g., an IM message) a hyperlink to the data (e.g., as provided by one or more sensors 176/178 and/or by mental state determination module 162) indicative of the inferred mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) of the authoring user 130.

In the same or alternative embodiments, the association operation 304 may further include a pairing operation 610 for pairing an identity of the electronic message with the data indicative of the inferred mental state of the authoring user. For example, in some implementations, the pairing operation 610 may include the authoring network device 104 pairing (e.g., via the association module 164) an identity (e.g., a symbolic, numeric, and/or textural representation) of the electronic message (e.g., an email message) with the data (e.g., as provided by one or more sensors 176/178 and/or by mental state determination module 162) indicative of the inferred mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity).

In some embodiments, the pairing operation 610 may further include an operation 612 for incorporating the data indicative of the inferred mental state and the identity of the electronic message into another electronic message. For instance, in some implementations, operation 612 may include the authoring network device 104 incorporating (e.g., via the association module 164) the data (e.g., as provided by one or more sensors 176/178 and/or by mental state determination module 162) indicative of the inferred mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) and the identity (e.g., as provided by an email application 172) of the electronic message (e.g., an email message to be transmitted via the wireless and/or wireless network[s] 108) into another electronic message (e.g., another email message to be transmitted via the wireless and/or wireless network[s] 108).

Figure 7A:
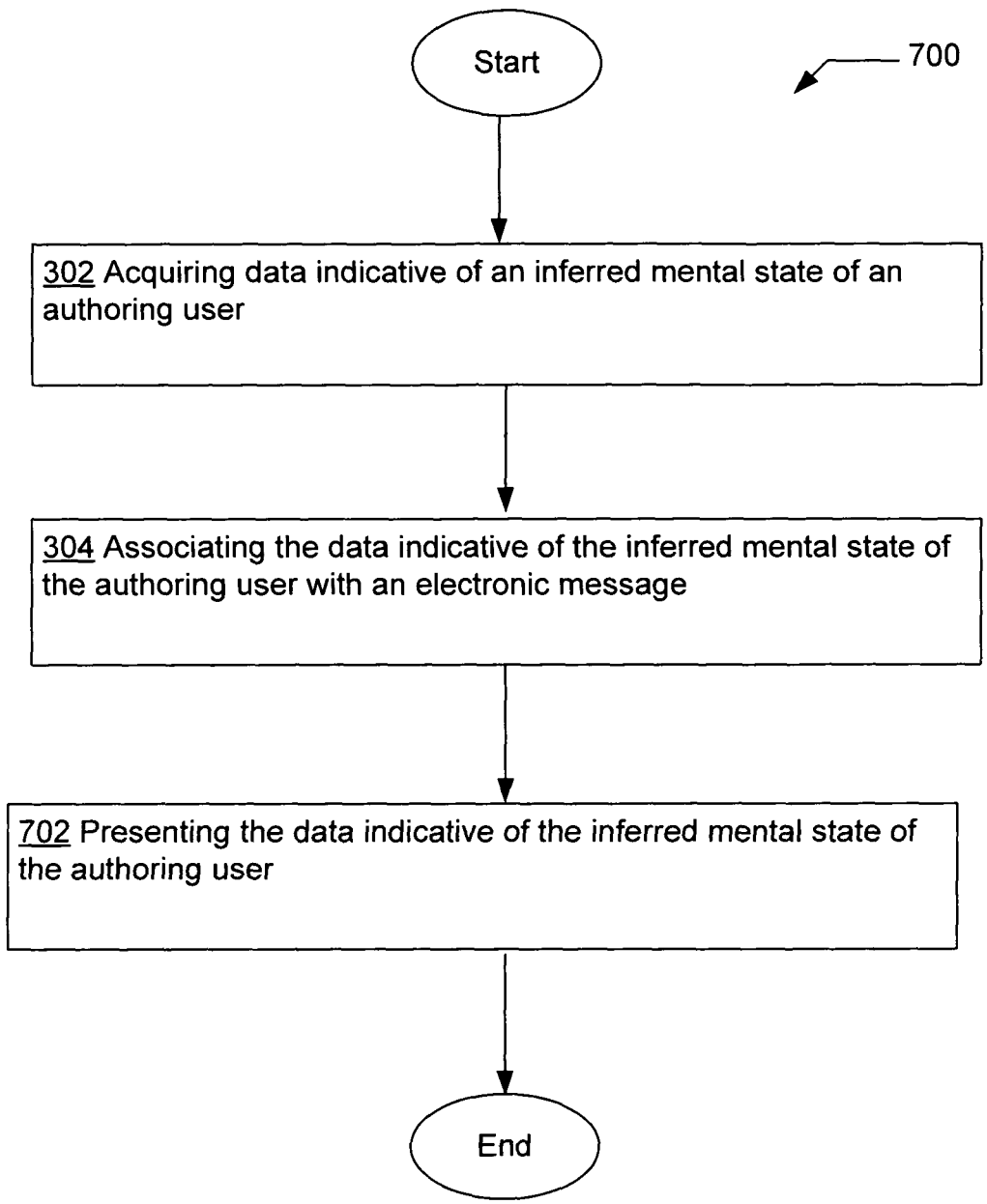
FIG. 7A is a high-level logic flowchart of an alternative process.

FIG. 7A illustrates another operational flow 700 in accordance with various embodiments. In particular, operational flow 700, which is similar (e.g., also having an acquisition operation 302 and an association operation 304 as described previously) to operational flow 300 of FIG. 3, includes a presentation operation 702 for presenting the data indicative of the inferred mental state of the authoring user in addition to the previously described operations (e.g., acquisition operation 302 and association operation 304). For instance, in some implementations, the presentation operation 702 may include the authoring network device 130 of FIG. 1 presenting (e.g., via the presentation module 160 and through user interface 170 and/or network communication interface 174) the data (e.g., as provided by one or more sensors 176/178 and/or by mental state determination module 162) indicative of the inferred mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) of the authoring user 130.

Figure 7B:
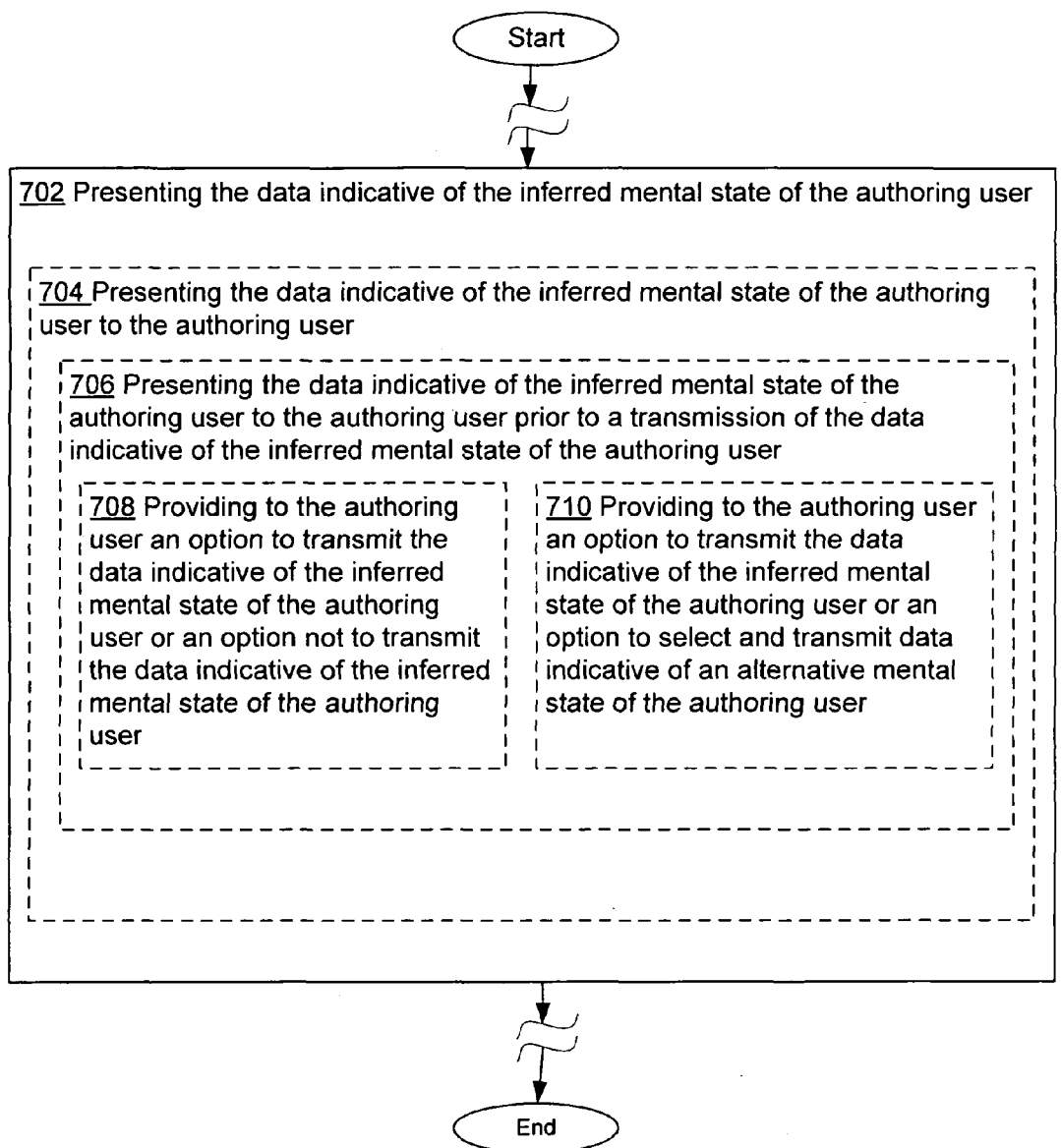
FIG. 7B is a high-level logic flowchart of a process depicting alternate implementations of presentation operation 702 of FIG. 7A.

FIG. 7B illustrates various embodiments of the presentation operation 702 of FIG. 7A. More particularly, FIG. 7B illustrates example embodiments where the presentation operation 702 includes one or more additional operations. For example, in some embodiments, the presentation operation 702 may include an operation 704 for presenting the data indicative of the inferred mental state of the authoring user to the authoring user. For instance, in some implementations, operation 704 may include the authoring network device 130 of FIG. 1 presenting (e.g., as performed by the presentation module 166) the data (e.g., as provided by one or more sensors 176/178 and/or by mental state determination module 162) indicative of the inferred mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) of the authoring user 130 to the authoring user 130 (e.g., via the user interface 170).

In various embodiments, operation 704 may further include an example operation 706 for presenting the data indicative of the inferred mental state of the authoring user to the authoring user prior to a transmission of the data indicative of the inferred mental state of the authoring user. For instance, in some implementations, the example operation 706 may include the authoring network device 130 presenting (e.g., via email application 172) the data (e.g., as provided by one or more sensors 176/178 and/or by mental state determination module 162) indicative of the inferred mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) of the authoring user 130 to the authoring user 130 via the user interface 170 prior to a transmission (e.g., via the network communication interface 174) of the data indicative of the inferred mental state of the authoring user 130.

In some alternative or the same embodiments, the example operation 706 may include one or more additional operations. For example, in some embodiments, the example operation 706 may include an operation 708 for providing to the authoring user at least one of an option to transmit the data indicative of the inferred mental state of the authoring user or an option not to transmit the data indicative of the inferred mental state of the authoring user. For instance, in some implementations, operation 708 may include the authoring network device 130 of FIG. 1 providing (e.g., via the presentation module 166 and user interface 170) to the authoring user 130 at least one of an option to transmit (e.g., via the network communication interface 174) the data (e.g., as provided by one or more sensors 176/178 and/or by mental state determination module 162) indicative of the inferred mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) of the authoring user 130 or an option not to transmit the data indicative of the inferred mental state of the authoring user 130.

Figure 7C:
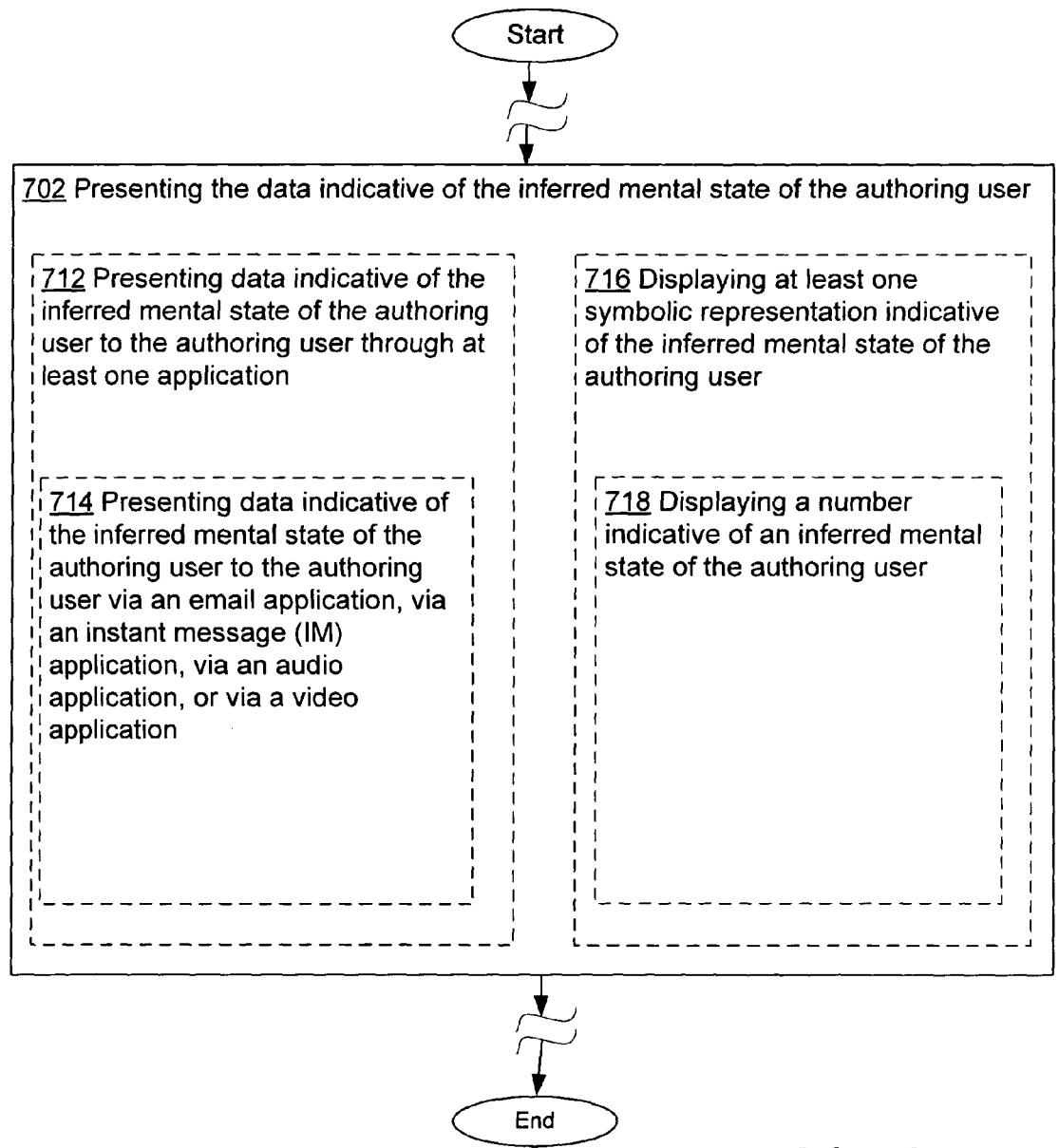
FIG. 7C is a high-level logic flowchart of a process depicting alternate implementations of presentation operation 702 of FIG. 7A.

FIG. 7C illustrates various alternative embodiments of the presentation operation 702 of FIG. 7A. More particular, FIG. 7C illustrates additional example embodiments where the presentation operation 702 includes additional one or more operations. For example, in some embodiments, the presentation operation 702 may include an operation 712 for presenting data indicative of the inferred mental state of the authoring user to the authoring user through at least one application. For instance, in some implementations, operation 712 may include the authoring network device 104 of FIG. 1 presenting (e.g., via the presentation module 166) data indicative of the inferred mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) of the authoring user 130 to the authoring user 130 (e.g., via the user interface 170) through at least one application (e.g., a network communication application).

In various embodiments, operation 712 may include an operation 714 for presenting data indicative of the inferred mental state of the authoring user to the authoring user via an email application, via an instant message (IM) application, via an audio application, or via a video application. For instance, in some implementations, operation 714 may include the authoring network device 104 and the presentation module 166 presenting data (e.g., as provided by one or more sensors 176/178 and/or by mental state determination module 162) indicative of the inferred mental state (e.g., state of anger, state of distress, state of pain, state of frustration, state of approval or disapproval, state of trust, state of fear, and/or state of happiness) of the authoring user 130 to the authoring user 130 (e.g., through user interface 170) via an email application, via an instant message (IM) application, via an audio application, or via a video application.

In some alternative or the same embodiments, the presentation operation 702 may also include an operation 716 for displaying at least one symbolic representation indicative of the inferred mental state of the authoring user. For instance, in some implementations, operation 716 may include the authoring network device 104 displaying (e.g., via the user interface 170) at least one symbolic representation (e.g., a number, a letter, an icon, an image, a word, a phrase, or other symbolic representation) indicative of the inferred mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) of the authoring user 130.

In various embodiments, operation 716 may include operation 718 for displaying a number indicative of an inferred mental state of the authoring user. For instance, in some implementations, operation 718 may include the authoring network device 104 displaying (e.g., via the user interface 170 such as a display monitor) a number indicative of an inferred mental state (e.g., state of anger, state of distress, state of pain, state of frustration, state of approval or disapproval, state of trust, state of fear state of happiness, state of surprise, state of inattention, state of arousal, state of impatience, state of confusion, state of distraction, state of overall mental activity, state of alertness, and/or state of acuity) of the authoring user 130.

Figure 8A:
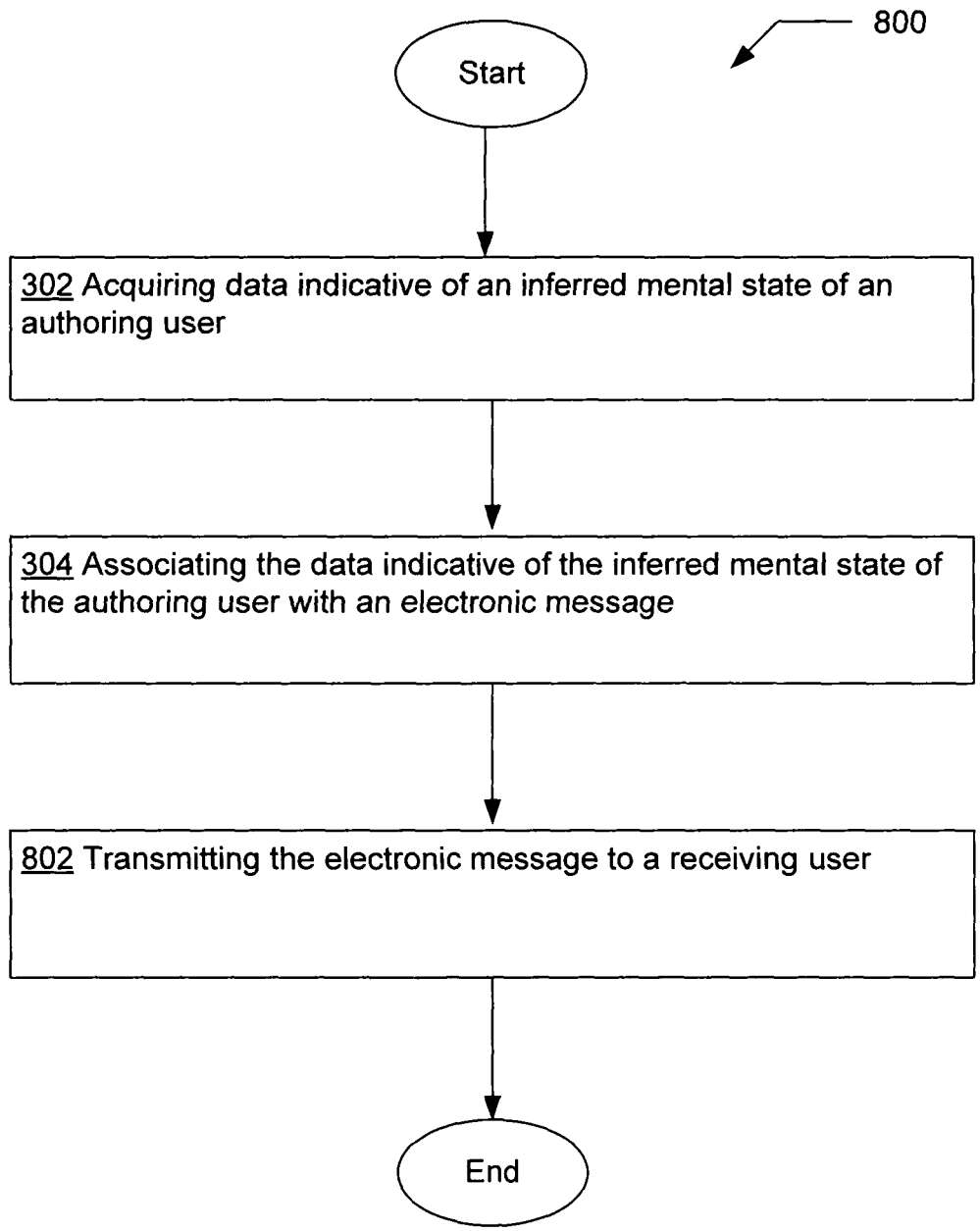
FIG. 8A is a high-level logic flowchart of another alternative process.

FIG. 8A illustrates still another operational flow 800 in accordance with various embodiments. In particular, operational flow 800, which is similar (e.g., also having an acquisition operation 302 and an association operation 304 as described previously) to operational flow 300 of FIG. 3, includes a transmission operation 802 for transmitting the electronic message to a receiving user. For instance, in some implementations, operation 802 may include the authoring network device 104 of FIG. 1 transmitting (e.g., via the network communication interface 174) the electronic message (e.g., an email, an IM message, an audio message, and/or a video message) to a receiving user 120 (e.g., via the receiving network device 102).

Figure 8B:
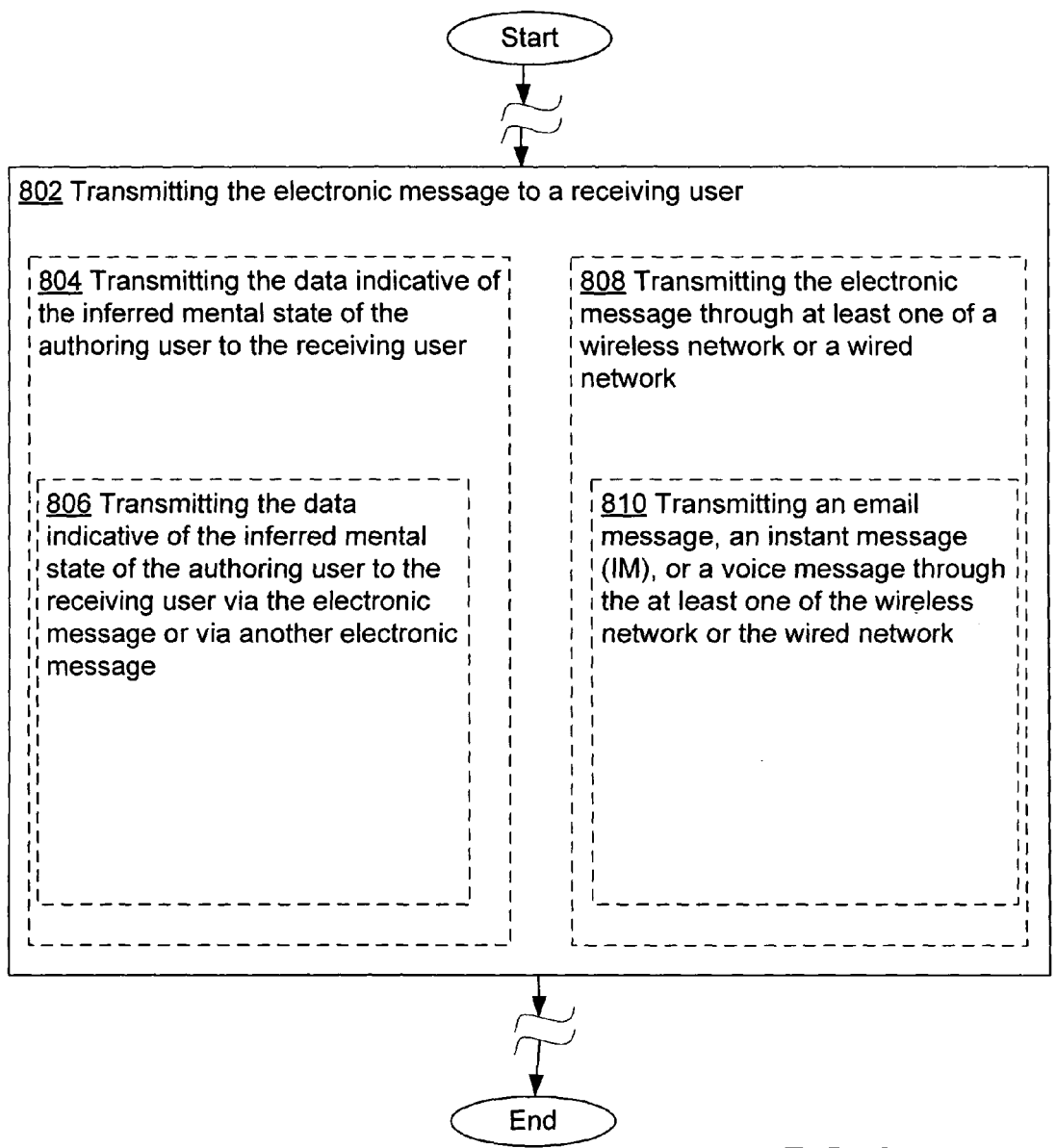
FIG. 8B is a high-level logic flowchart of a process depicting alternate implementations of transmission operation 802 of FIG. 8A.

FIG. 8B illustrates various embodiments of the transmission operation 802 of FIG. 8A. More particularly, FIG. 8B illustrates example embodiments where the transmission operation 802 includes one or more additional operations. For example, in some embodiments, the transmission operation 802 may include operation 804 for transmitting the data indicative of the inferred mental state of the authoring user to the receiving user. For instance, in some implementations, operation 804 may include the authoring network device 104 of FIG. 1 transmitting (e.g., via the transmission module 168) the data (e.g., as provided by one or more sensors 176/178 and/or by mental state determination module 162) indicative of the inferred mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) of the authoring user 130 to the receiving user 120 (e.g., via the wireless and/or wired network[s] 108).

In various embodiments, operation 804 may further include an example operation 806 for transmitting the data indicative of the inferred mental state of the authoring user to the receiving user via the electronic message or via another electronic message. For instance, in some implementations, operation 806 may include the authoring network device 104 transmitting (e.g., via the transmission module 168) the data (e.g., as provided by one or more sensors 176/178 and/or by mental state determination module 162) indicative of the inferred mental state (e.g., state of anger, state of distress, state of pain, state of frustration, state of approval or disapproval, state of trust, state of fear, state of happiness, state of surprise, state of inattention, state of arousal, state of impatience, state of confusion, state of distraction, state of overall mental activity, state of alertness, and/or state of acuity) of the authoring user 130 to the receiving user 120 via the electronic message 150 (e.g., a first email message) or via another electronic message (e.g., a second email message or in another electronic message other than an email message).

In the same or alternative embodiments, the transmission operation 802 may include an operation 808 for transmitting the electronic message through at least one of a wireless network or a wired network. For instance, in some implementations, operation 808 may include the authoring network device 104 of FIG. 1 transmitting (e.g., via the transmission module 168 employing an IM application 172 and the network communication interface 174) the electronic message (e.g., IM message) through at least one of a wireless network and/or a wired network[s] 108.

In various embodiments, operation 808 may further include an operation 810 for transmitting an email message, an instant message (IM), an audio message, or a video message through the at least one of the wireless network or the wired network. For instance, in some implementations, operation 810 includes the authoring network device 104 transmitting (e.g., via the transmission module 168 using the network communication interface 174) an email message, an instant message (IM), an audio message, or a video message through the at least one of the wireless and/or the wired network[s] 108.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware in one or more machines or articles of manufacture), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation that is implemented in one or more machines or articles of manufacture; or, yet again alternatively, the implementer may opt for some combination of hardware, software, and/or firmware in one or more machines or articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware in one or more machines or articles of manufacture.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A computationally-implemented method, comprising:
    acquiring, by a network device, data indicative of an inferred mental state of an authoring user, wherein said acquiring data indicative of an inferred mental state of an authoring user comprises:
        determining the data indicative of the inferred mental state of the authoring user, wherein said determining the data indicative of the inferred mental state of the authoring user comprises:
            determining a result of an observation of one or more physical characteristics of the authoring user, the observation of the one or more physical characteristics of the authoring user being performed during or proximate to a composition by the authoring user of an electronic message, wherein said determining a result of an observation of one or more physical characteristics of the authoring user, the observation of the one or more physical characteristics of the authoring user being performed during or proximate to a composition by the authoring user of an electronic message comprises:
                sensing the one or more physical characteristics of the authoring user in a response associated with a functional near infrared procedure on the authoring user; and
    associating the data indicative of the inferred mental state of the authoring user with the electronic message, wherein said associating the data indicative of the inferred mental state of the authoring user with an electronic message includes at least:
        associating the data indicative of the inferred mental state of the authoring user with an electronic message, the data indicative of the inferred mental state of the authoring user being raw sensor provided data indicating brain characteristics of the authoring user.

2. A computationally-implemented method, comprising:
    acquiring, by a network device, data indicative of an inferred mental state of an authoring user, wherein said acquiring data indicative of an inferred mental state of an authoring user comprises:
        determining the data indicative of the inferred mental state of the authoring user, wherein said determining the data indicative of the inferred mental state of the authoring user comprises:
            determining a result of an observation of one or more physical characteristics of the authoring user, the observation of the one or more physical characteristics of the authoring user being performed during or proximate to a composition by the authoring user of an electronic message, wherein said determining a result of an observation of one or more physical characteristics of the authoring user, the observation of the one or more physical characteristics of the authoring user being performed during or proximate to a composition by the authoring user of an electronic message comprises:
                sensing the one or more physical characteristics of the authoring user in a response associated with a functional near infrared procedure on the authoring user; and
    associating the data indicative of the inferred mental state of the authoring user with the electronic message, wherein said associating the data indicative of the inferred mental state of the authoring user with an electronic message includes at least:
associating the data indicative of the inferred mental state of the authoring user with an electronic message, the data indicative of the inferred mental state of the authoring user being raw sensor provided data indicating brain characteristics of the authoring user, wherein said associating the data indicative of the inferred mental state of the authoring user with an electronic message, the data indicative of the inferred mental state of the authoring user being raw sensor provided data indicating brain characteristics of the authoring user includes at least:
associating the data indicative of the inferred mental state of the authoring user with an electronic message, the data indicative of the inferred mental state of the authoring user being raw sensor provided data indicating brain characteristics of the authoring user that was obtained using a functional near infrared device.

3. A computationally-implemented method, comprising:
acquiring, by a network device, data indicative of an inferred mental state of an authoring user, wherein said acquiring data indicative of an inferred mental state of an authoring user comprises:
determining the data indicative of the inferred mental state of the authoring user, wherein said determining the data indicative of the inferred mental state of the authoring user comprises:
determining a result of an observation of one or more physical characteristics of the authoring user, the observation of the one or more physical characteristics of the authoring user being performed during or proximate to a composition by the authoring user of an electronic message, wherein said determining a result of an observation of one or more physical characteristics of the authoring user, the observation of the one or more physical characteristics of the authoring user being performed during or proximate to a composition by the authoring user of an electronic message comprises:
sensing the one or more physical characteristics of the authoring user in a response associated with a functional near infrared procedure on the authoring user; and
associating the data indicative of the inferred mental state of the authoring user with the electronic message, wherein said associating the data indicative of the inferred mental state of the authoring user with an electronic message includes at least:
associating the data indicative of the inferred mental state of the authoring user with an electronic message, the data indicative of the inferred mental state of the authoring user being raw sensor provided data indicating brain characteristics of the authoring user, wherein said associating the data indicative of the inferred mental state of the authoring user with an electronic message, the data indicative of the inferred mental state of the authoring user being raw sensor provided data indicating brain characteristics of the authoring user includes at least:
associating the data indicative of the inferred mental state of the authoring user with an electronic message, the data indicative of the inferred mental state of the authoring user being raw sensor provided data indicating brain characteristics of the authoring user that was obtained using a functional near infrared device, wherein said associating the data indicative of the inferred mental state of the authoring user with an electronic message, the data indicative of the inferred mental state of the authoring user being raw sensor provided data indicating brain characteristics of the authoring user that was obtained using a functional near infrared device includes at least:
associating the data indicative of the inferred mental state of the authoring user with an electronic message, the data indicative of the inferred mental state of the authoring user being raw sensor provided data indicating brain characteristics of the authoring user that was obtained using a functional near infrared device to sense brain activities of the authoring user during or proximate to the composition of the electronic message.

4. A computationally-implemented system, comprising:
means for acquiring data indicative of an inferred mental state of an authoring user, wherein said means for acquiring data indicative of an inferred mental state of an authoring user comprises:
means for determining the data indicative of the inferred mental state of the authoring user, wherein said means for determining the data indicative of the inferred mental state of the authoring user comprises:
means for determining a result of an observation of one or more physical characteristics of the authoring user, the observation of the one or more physical characteristics of the authoring user being performed during or proximate to a composition by the authoring user of an electronic message, wherein said means for determining a result of an observation of one or more physical characteristics of the authoring user, the observation of the one or more physical characteristics of the authoring user being performed during or proximate to a composition by the authoring user of an electronic message comprises:
means for sensing the one or more physical characteristics of the authoring user in a response associated with a functional near infrared procedure on the authoring user; and
means for associating the data indicative of the inferred mental state of the authoring user with the electronic message, wherein said means for associating the data indicative of the inferred mental state of the authoring user with an electronic message includes at least:
means for associating the data indicative of the inferred mental state of the authoring user with an electronic message, the data indicative of the inferred mental state of the authoring user being raw sensor provided data indicating brain characteristics of the authoring user.

5. A computationally-implemented system, comprising:
means for acquiring data indicative of an inferred mental state of an authoring user, wherein said means for acquiring data indicative of an inferred mental state of an authoring user comprises:
means for determining the data indicative of the inferred mental state of the authoring user, wherein said means for determining the data indicative of the inferred mental state of the authoring user comprises:
means for determining a result of an observation of one or more physical characteristics of the authoring user, the observation of the one or more physical characteristics of the authoring user being performed during or proximate to a composition by the authoring user of an electronic message, wherein said means for determining a result of an observation of one or more physical characteristics of the authoring user, the observation of the one or more physical characteristics of the authoring user being performed during or proximate to a composition by the authoring user of an electronic message comprises:
  means for sensing the one or more physical characteristics of the authoring user in a response associated with a functional near infrared procedure on the authoring user; and
means for associating the data indicative of the inferred mental state of the authoring user with the electronic message, wherein said means for associating the data indicative of the inferred mental state of the authoring user with an electronic message includes at least:
  means for associating the data indicative of the inferred mental state of the authoring user with an electronic message, the data indicative of the inferred mental state of the authoring user being raw sensor provided data indicating brain characteristics of the authoring user, wherein said means for associating the data indicative of the inferred mental state of the authoring user with an electronic message, the data indicative of the inferred mental state of the authoring user being raw sensor provided data indicating brain characteristics of the authoring user includes at least:
    means for associating the data indicative of the inferred mental state of the authoring user with an electronic message, the data indicative of the inferred mental state of the authoring user being raw sensor provided data indicating brain characteristics of the authoring user that was obtained using a functional near infrared device.

6. A computationally-implemented system, comprising:
means for acquiring data indicative of an inferred mental state of an authoring user, wherein said means for acquiring data indicative of an inferred mental state of an authoring user comprises:
  means for determining the data indicative of the inferred mental state of the authoring user, wherein said means for determining the data indicative of the inferred mental state of the authoring user comprises:
    means for determining a result of an observation of one or more physical characteristics of the authoring user, the observation of the one or more physical characteristics of the authoring user being performed during or proximate to a composition by the authoring user of an electronic message, wherein said means for determining a result of an observation of one or more physical characteristics of the authoring user, the observation of the one or more physical characteristics of the authoring user being performed during or proximate to a composition by the authoring user of an electronic message comprises:
      means for sensing the one or more physical characteristics of the authoring user in a response associated with a functional near infrared procedure on the authoring user; and
means for associating the data indicative of the inferred mental state of the authoring user with the electronic message, wherein said means for associating the data indicative of the inferred mental state of the authoring user with an electronic message includes at least:
  means for associating the data indicative of the inferred mental state of the authoring user with an electronic message, the data indicative of the inferred mental state of the authoring user being raw sensor provided data indicating brain characteristics of the authoring user, wherein said means for associating the data indicative of the inferred mental state of the authoring user with an electronic message, the data indicative of the inferred mental state of the authoring user being raw sensor provided data indicating brain characteristics of the authoring user includes at least:
    means for associating the data indicative of the inferred mental state of the authoring user with an electronic message, the data indicative of the inferred mental state of the authoring user being raw sensor provided data indicating brain characteristics of the authoring user that was obtained using a functional near infrared device, wherein said means for associating the data indicative of the inferred mental state of the authoring user with an electronic message, the data indicative of the inferred mental state of the authoring user being raw sensor provided data indicating brain characteristics of the authoring user that was obtained using a functional near infrared device includes at least:
      means for associating the data indicative of the inferred mental state of the authoring user with an electronic message, the data indicative of the inferred mental state of the authoring user being raw sensor provided data indicating brain characteristics of the authoring user that was obtained using a functional near infrared device to sense brain activities of the authoring user during or proximate to the composition of the electronic message.

* * * * *

UNITED STATES PATENT AND TRADEMARK OFFICE
CERTIFICATE OF CORRECTION

PATENT NO. : 9,101,263 B2
APPLICATION NO. : 12/215683
DATED : August 11, 2015
INVENTOR(S) : Edward K. Y. Jung et al.

Page 1 of 1

It is certified that error appears in the above-identified patent and that said Letters Patent is hereby corrected as shown below:

Specification:

Column 1, Lines 64-67 through Column 2, Lines 1-6,
Fifth Paragraph Under the "RELATED APPLICATIONS" section:

"For purposes of the USPTO extra-statutory requirements, the present application is related to TICULAR ASSOCIATION OF INFERENCE DATA INDICATIVE OF AN INFERRED MENTAL STATE OF AN AUTHORING USER AND SOURCE IDENTITY DATA, naming Edward K.Y. Jung, Eric C. Leuthardt, Royce A. Levien, Robert W. Lord, Mark A. Malamud, John D. Rinaldo, Jr. and Lowell L. Wood, Jr. as inventors, filed 29 Aug. 2008, which is currently co-pending, or is an application of which a currently co-pending application is entitled to the benefit of the filing date."

Should read:

-- For purposes of the USPTO extra-statutory requirements, the present application is related to U.S. patent application Ser. No. 13/135,462, entitled ACQUISITION AND PRESENTATION OF DATA INDICATIVE OF AN EXTENT OF CONGRUENCE BETWEEN INFERRED MENTAL STATES OF AUTHORING USERS, naming Edward K.Y. Jung, Eric C. Leuthardt, Royce A. Levien, Robert W. Lord, Mark A. Malamud, John D. Rinaldo, Jr. and Lowell L. Wood, Jr. as inventors, filed 05 July 2011, which is currently co-pending, or is an application of which a currently co-pending application is entitled to the benefit of the filing date. --

Signed and Sealed this
Twenty-first Day of June, 2016

Michelle K. Lee
*Director of the United States Patent and Trademark Office*